(12) United States Patent
Shin et al.

(10) Patent No.: US 11,597,842 B2
(45) Date of Patent: Mar. 7, 2023

(54) LABELING DYE AND KIT INCLUDING SAME

(71) Applicant: SFC CO., LTD., Cheongju-si (KR)

(72) Inventors: Bong-Ki Shin, Cheongju-si (KR);
Tae-Young Kim, Cheongju-si (KR);
Ju-Man Song, Cheongju-si (KR);
Hee-Jung Yang, Cheongju-si (KR);
Jong-Tae Je, Cheongju-si (KR)

(73) Assignee: SFC CO., LTD., Cheongju-si (KR)

( * ) Notice: Subject to any disclaimer, the term of this patent is extended or adjusted under 35 U.S.C. 154(b) by 311 days.

(21) Appl. No.: 16/860,982

(22) Filed: Apr. 28, 2020

(65) Prior Publication Data

US 2020/0255668 A1 Aug. 13, 2020

Related U.S. Application Data

(63) Continuation of application No. PCT/KR2018/014104, filed on Nov. 16, 2018.

(30) Foreign Application Priority Data

Nov. 16, 2017 (KR) .................. 10-2017-0153074
Nov. 7, 2018 (KR) .................. 10-2018-0135720

(51) Int. Cl.
| | | |
|---|---|---|
| *C09B 23/00* | (2006.01) | |
| *C09B 57/02* | (2006.01) | |
| *C09B 23/01* | (2006.01) | |
| *G01N 33/58* | (2006.01) | |

(52) U.S. Cl.
CPC .......... *C09B 23/0075* (2013.01); *C09B 57/02* (2013.01); *G01N 33/582* (2013.01)

(58) Field of Classification Search
CPC ...................................... C09B 57/02
See application file for complete search history.

(56) References Cited

U.S. PATENT DOCUMENTS

2018/0203015 A1* 7/2018 Song ................... C09B 68/00

FOREIGN PATENT DOCUMENTS

| KR | 10-2010-0115301 A | 10/2010 |
|---|---|---|
| KR | 10-2017-0009795 A | 1/2017 |
| KR | 10-2017-0026245 A | 3/2017 |
| KR | 10-2017-0101360 A | 9/2017 |
| KR | 10-2017-0105662 A | 9/2017 |

OTHER PUBLICATIONS

Song, et al. WO 2017010852 abstract (Accesssion No. 2017:116419) Jan. 19, 2017; retrieved from STN.*
International Search Report issued in PCT/KR2018/014104; dated May 23, 2019.
Jean-Alexandre Richard et al, Synthesis of N,N-Dialkylamino-nor-Dihydroxanthene-Hemicyanine Fused Near-Infrared Fluorophores and Their First Water-Soluble and/or Bioconjugatable Analogues, Chem. Asian J., 10.1002/asia.201700176, pp. 1-13.

* cited by examiner

*Primary Examiner* — Shawquia Jackson
(74) *Attorney, Agent, or Firm* — Studebaker & Brackett PC

(57) ABSTRACT

The present invention relates to: a labeling dye having excellent fluorescent intensity and photostability; and a kit.

17 Claims, 5 Drawing Sheets

LABELING DYE AND KIT INCLUDING SAME

CROSS-REFERENCE TO RELATED APPLICATIONS

The present application is a continuation of International Patent Application No. PCT/KR2018/014104 filed on Nov. 16, 2018, which in turn claims the benefit of Korean Application No. 10-2017-0153074, filed on Nov. 16, 2017 and Korean Application No. 10-2018-0135720, filed on Nov. 7, 2018, the disclosures of which are incorporated by reference into the present application.

TECHNICAL FIELD

The present invention relates to: a labeling dye having excellent fluorescent intensity and photostability; and a kit.

This research was supported by a grant from the Advanced Technology Center (ATC) Program (10076988, Development of fluorescent materials and their application technologies for molecular diagnosis) funded by the Ministry of Trade, Industry & Energy of the Republic of Korea.

BACKGROUND ART

Fluorescence is the most commonly used technique for non-destructively tracking or analyzing biological molecules in the field of life science.

Although there are biomolecules which emit light independently, such as a green fluorescent protein (GFP), generally, after biological tissues or cells and biological materials at lower levels are stained with fluorescent dyes, or biological molecules such as proteins and nucleic acids are labeled with fluorescent dyes, an accompanying optical system can detect a fluorescence signal, thereby obtaining visualized data by various techniques.

In order to apply fluorescent dyes, those, which have low photobleaching and quenching and a high molecular extinction coefficient and quantum efficiency when generally present in a medium in which most of the biomolecules are present, that is, an aqueous solution and are stable under various pH conditions, are preferred.

Although various fluorescent dyes have been used in various research areas, fluorescent dyes which satisfy the above-described conditions are extremely rare.

As the background art related to the present invention, there is Korean Patent Application Laid-Open No. 10-2017-0026245 (published on Mar. 8, 2017), and the aforementioned document discloses a perylene-based compound, a method for preparing the same, and a fluorescent dye including the same.

DISCLOSURE

Technical Problem

An object of the present invention is to provide a labeling dye having excellent fluorescent intensity and photostability.

Further, an object of the present invention is to provide a kit including the labeling dye.

Technical Solution

According to an aspect of the present invention, provided is a labeling dye represented by the following [Chemical Formula 1] or [Chemical Formula 2].

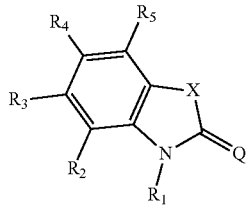

[Chemical Formula 1]

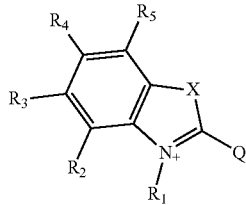

[Chemical Formula 2]

wherein,

X is $CR_6R_7$, S, or O,

Q is a polymethine in which a ring selectively including at least one heteroatom selected from nitrogen, oxygen, and sulfur is substituted, or a polyene in which a ring selectively including at least one heteroatom selected from nitrogen, oxygen, and sulfur is substituted, $R_1$ to $R_7$ are each independently selected from hydrogen, deuterium, a substituted or unsubstituted C1-C10 alkyl, a substituted or unsubstituted C1-C10 heteroalkyl including at least one heteroatom, a substituted or unsubstituted C2-C10 alkenyl, a substituted or unsubstituted C2-C10 alkynyl, a substituted or unsubstituted C1-C10 alkoxy, a substituted or unsubstituted aryloxy, a substituted or unsubstituted C1-C10 haloalkyl, a halogen, cyano, hydroxyl, a substituted or unsubstituted amino, a substituted or unsubstituted amide, carbamates, sulfhydryl, nitro, carboxyl, carboxylates, a substituted or unsubstituted aryl, a substituted or unsubstituted heteroaryl, a substituted or unsubstituted aralkyl, quaternary ammonium, phosphoric acid, phosphates, ketones (—CO), aldehydes, esters (—COO), acyl chloride, sulfonic acid, sulfonates, hydrazine, thiols, acetals, ketals, phosphonates (phosphites), hypophosphite, sulfohydroxyl, sulfates, azido, guanidium, carbonyl, thiocarbonyl, aminothiocarbonyl, polyalkylene oxides, a -L-X functional group, a -L-Z functional group, and the following [Chemical Formula 3] to [Chemical Formula 5], or two or more selected from $R_1$ to $R_7$ are linked to each other to form a fused ring, L is a linker including 1 to 150 non-hydrogen atoms, X is a reactive group, Z is a fluorophore capable of generating a fluorescence signal, at least one or more of $R_1$ to $R_7$ are one selected from the following [Chemical Formula 3] to [Chemical Formula 5],

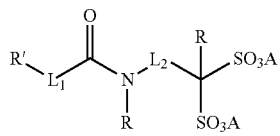

[Chemical Formula 3]

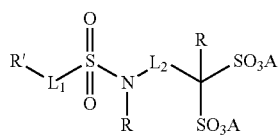

[Chemical Formula 4]

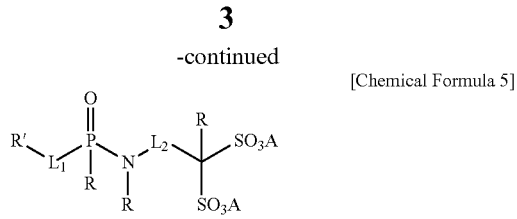

in [Chemical Formula 3] to [Chemical Formula 5], $L_1$ is a linker including 1 to 150 non-hydrogen atoms, $L_1$ in [Chemical Formula 3] to [Chemical Formula 5] is present or not present, $L_2$ is a C1-C20 alkylene, or a C1-C20 heteroalkylene including at least one heteroatom, A is hydrogen or $M^+$ ($M^+$ is a counter ion), R is selected from hydrogen, a substituted or unsubstituted C1-C10 alkyl, a substituted or unsubstituted C1-C10 heteroalkyl including at least one heteroatom, a substituted or unsubstituted C2-C10 alkenyl, a substituted or unsubstituted C2-C10 alkynyl, a substituted or unsubstituted C1-C10 alkoxy, and a substituted or unsubstituted C1-C10 haloalkyl, R' represents a site bonded to at least one of $R_1$ to $R_7$, and at least one or more of R and $R_1$ to $R_7$ are a -L-X functional group.

Further, according to another aspect of the present, provided is a kit including the labeling dye.

Advantageous Effects

The labeling dye according to the present invention has excellent light characteristics such as fluorescent intensity and photostability, and thus can be usefully used for a kit for labeling biomolecules, and the like.

MODES OF THE INVENTION

Figure 1:
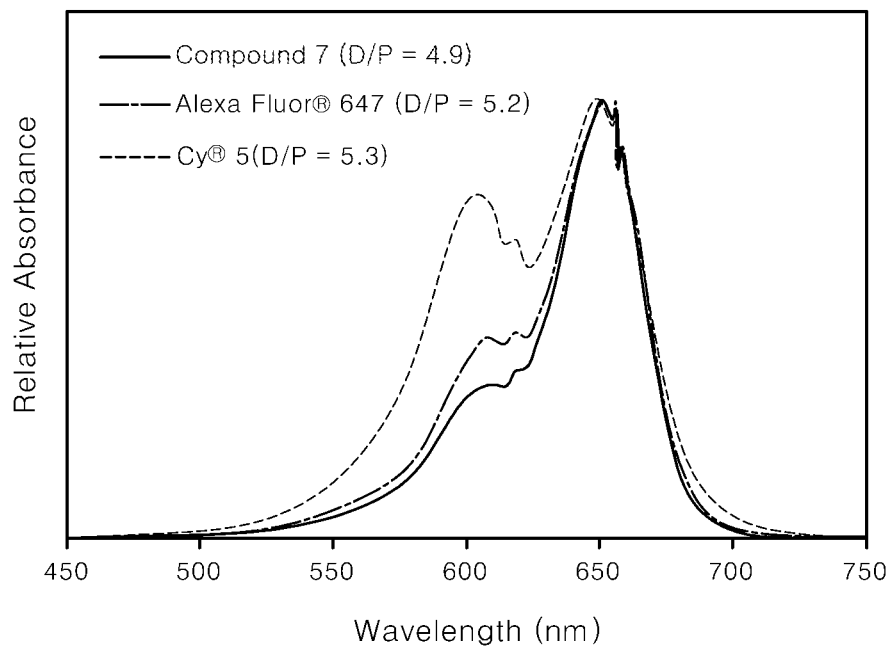
FIGS. 1 and 2 are graphs comparing the normalized maximum absorption wavelength and the normalized maximum fluorescence wavelength of each of antibody conjugates having similar D/P ratios.

The benefits and features of the present application, and the methods of achieving the benefits and features will become apparent with reference to Examples to be described below in detail along with the accompanying drawings. However, the present invention is not limited to the Examples to be disclosed below and may be implemented in various other forms, and the present Examples are only provided for rendering the disclosure of the present invention complete and for fully representing the scope of the invention to a person with ordinary skill in the technical field to which the present invention pertains, and the present invention will be defined only by the scope of the claims. Throughout the specification, like reference numerals indicate like constituent elements.

Hereinafter, a labeling dye according to preferred exemplary embodiments of the present invention and a kit including the same will be described in reference to the accompanying drawings.

According to an aspect of the present invention, provided is a labeling dye represented by the following [Chemical Formula 1] or [Chemical Formula 2].

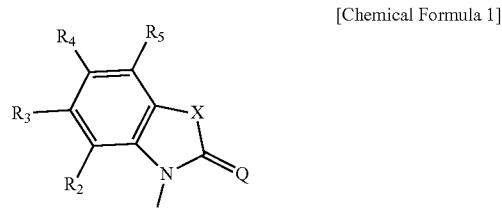

[Chemical Formula 1]

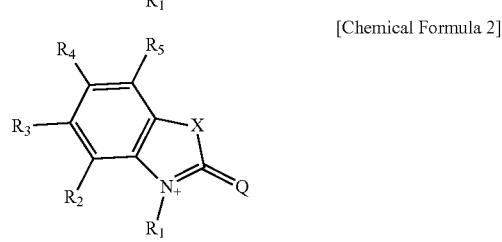

[Chemical Formula 2]

Here, X is $CR_6R_7$, S, or O, and Q is a polymethine in which a ring selectively including at least one heteroatom selected from nitrogen, oxygen, and sulfur is substituted, or a polyene in which a ring selectively including at least one heteroatom selected from nitrogen, oxygen, and sulfur is substituted, and the polymethine is a compound consisting of an odd number of methine groups which are bound by alternating single and double bonds, and the polyene is a compound consisting of an even number of methine groups.

Any carbon in the polymethine or polyene in which the ring selectively including the heteroatom is substituted may be substituted with at least one substituent, and adjacent substituents may be linked to each other to form a ring.

In an exemplary embodiment, the substituent substituting any carbon in a polymethine or polyene may be selected from hydrogen, deuterium, a substituted or unsubstituted C1-C10 alkyl, a substituted or unsubstituted C1-C10 heteroalkyl including at least one heteroatom, a substituted or unsubstituted C2-C10 alkenyl, a substituted or unsubstituted C2-C10 alkynyl, a substituted or unsubstituted C1-C10 alkoxy, a substituted or unsubstituted aryloxy, a substituted or unsubstituted C1-C10 haloalkyl, a halogen, cyano, hydroxyl, a substituted or unsubstituted amino, a substituted or unsubstituted amide, carbamates, sulfhydryl, nitro, carboxyl, carboxylates, a substituted or unsubstituted aryl, a substituted or unsubstituted heteroaryl, a substituted or unsubstituted aralkyl, quaternary ammonium, phosphoric acid, phosphates, ketones (—CO), aldehydes, esters (—COO), acyl chloride, sulfonic acid, sulfonates, hydrazine, thiols, acetals, ketals, phosphonates (phosphites), hypophosphite, sulfohydroxyl, sulfates, azido, guanidium, carbonyl, thiocarbonyl, aminothiocarbonyl, polyalkylene oxides, a -L-X functional group, a -L-Z functional group, and the following [Chemical Formula 3] to [Chemical Formula 5].

In an exemplary embodiment, the following compounds may be specified by a substituent present in a polymethine or polyene.

First, adjacent substituents in a polymethine or polyene may be linked to each other to form a ring, thereby forming labeling dyes represented by [Compound 2], [Compound 11], [Compound 13], [Compound 17], and [Compound 28].

Second, a substituent in a polymethine or polyene and a substituent selected from $R_1$ to $R_7$ of [Chemical Formula 1] or [Chemical Formula 2] may be linked to each other to form a ring, thereby forming labeling dyes represented by [Compound 20], [Compound 21], and [Compound 52].

Third, a ring may be formed by satisfying both of the above-described first and second conditions, thereby forming labeling dyes represented by [Compound 22] to [Compound 24], [Compound 27], [Compound 46] to [Compound 51], and [Compound 53].

Fourth, the above-described third condition may be satisfied and simultaneously two or more selected from $R_2$ to $R_5$ of [Chemical Formula 1] or [Chemical Formula 2] may be linked to form a fused ring, thereby forming labeling dyes represented by [Compound 25] and [Compound 26].

In [Chemical Formula 1] or [Chemical Formula 2], $R_1$ to $R_7$ may be each independently selected from hydrogen, deuterium, a substituted or unsubstituted C1-C10 alkyl, a substituted or unsubstituted C1-C10 heteroalkyl including at least one heteroatom, a substituted or unsubstituted C2-C10 alkenyl, a substituted or unsubstituted C2-C10 alkynyl, a substituted or unsubstituted C1-C10 alkoxy, a substituted or unsubstituted aryloxy, a substituted or unsubstituted C1-C10 haloalkyl, a halogen, cyano, hydroxyl, a substituted or unsubstituted amino, a substituted or unsubstituted amide, carbamates, sulfhydryl, nitro, carboxyl, carboxylates, a substituted or unsubstituted aryl, a substituted or unsubstituted heteroaryl, a substituted or unsubstituted aralkyl, quaternary ammonium, phosphoric acid, phosphates, ketones (—CO), aldehydes, esters (—COO), acyl chloride, sulfonic acid, sulfonates, hydrazine, thiols, acetals, ketals, phosphonates (phosphites), hypophosphite, sulfohydroxyl, sulfates, azido, guanidium, carbonyl, thiocarbonyl, aminothiocarbonyl, polyalkylene oxides, a -L-X functional group, a -L-Z functional group, and the following [Chemical Formula 3] to [Chemical Formula 5], or two or more selected from $R_1$ to $R_7$ may be linked to each other to form a fused ring.

In the -L-X functional group and the -L-Z functional group, L is a linker including 1 to 150 non-hydrogen atoms, X is a reactive group, and Z is a fluorophore capable of generating a fluorescence signal.

As used herein, a Ca-Cb functional group refers to a functional group having a to b carbon atoms. For example, a Ca-Cb alkyl refers to a saturated aliphatic group having a to b carbon atoms, which includes a straight chain alkyl, a branched alkyl, and the like. Specifically, the alkyl may be methyl, ethyl, n-propyl, i-propyl, n-butyl, s-butyl, i-butyl, t-butyl, pent-1-yl, pent-2-yl, pent-3 -yl, 3 -methylbut-1-yl, 3 -methylbut-2-yl, 2-methylbut-2-yl, 2,2,2-trimethyleth- 1-yl, n-hexyl, n-heptyl, and n-octyl.

Further, as used herein, the alkoxy refers to both an —O-(alkyl) group and an —O-(unsubstituted cycloalkyl) group, and is a straight chain or branched hydrocarbon having one or more ether groups and 1 to 10 carbon atoms. Specific examples thereof include methoxy, ethoxy, propoxy, isopropoxy, n-butoxy, tert-butoxy, sec-butoxy, n-pentoxy, n-hexoxy, 1,2-dimethylbutoxy, cyclopropyloxy, cyclobutyloxy, cyclopentyloxy, cyclohexyloxy, and the like, but are not limited thereto.

Further, as used herein, the halogen refers to fluoro (—F), chloro (—Cl), bromo (—Br), or iodo (—I), and the haloalkyl refers to an alkyl substituted with the above-described halogen. For example, the halomethyl refers to a methyl (—$CH_2X$, —$CHX_2$, or —$CX_3$) in which at least one of hydrogens of a methyl is replaced with a halogen.

In the present invention, the aralkyl collectively refers to —$(CH_2)_n$Ar as a functional group in a form where an aryl is substituted with carbon of an alkyl. Examples of the aralkyl include benzyl (—$CH_2C_6H_5$), phenethyl (—$CH_2CH_2C_6H_5$), or the like.

A polyalkylene oxide may be further substituted, if necessary, as long as characteristics of the polymer are maintained. For example, the substitution may be a chemical bond for increasing or decreasing the chemical or biological stability of the polymer. As a specific example, any carbon or terminal carbon in the polyalkylene oxide may be substituted with hydroxyl, an alkyl ether (methyl ether, ethyl ether, propyl ether, and the like), carboxymethyl ether, carboxyethyl ether, benzyl ether, dibenzylmethylene ether, or dimethylamine.

The polyalkylene oxide may be a polyalkylene oxide (mPEG) terminated with an alkyl ether, and may be represented by a chemical formula of, for example, —$(CH_2CH_2O)_nCH_3$. Further, the polyalkylene oxide may be a polyalkylene oxide (mPEG) terminated with hydrogen, and may be represented by a chemical formula of, for example, —$(CH_2CH_2O)_nH$. The size of mPEG may vary depending on the size of n corresponding to the number of ethylene glycol repeating units.

In the -L-X functional group, L may be a linker including 1 to 150 non-hydrogen atoms, and X may be a reactive group selected from carboxyl, succinimidyl ester, sulfo-succinimidyl ester, isothiocyanate, maleimide, haloacetamide, hydrazide, vinyl sulphone, dichlorotriazine, phosphoramidite, alkyl halides, acyl halides, carbohydrazide, hydroxylamine, ketones, alkynes, azide, aliphatic and aromatic amines, sulfotetrafluorophenyl ester, sulfodichlorophenyl ester, carbonyl azide, sulfonyl chloride, sulfonyl fluoride, boronic acid, isocyanate, a halogen-substituted triazine, a halogen-substituted pyridine, a halogen-substituted diazine, tetrafluorophenyl ester, imido ester, azidonitrophenyl, glyoxal, and aldehyde.

In the -L-Z functional group, L is a linker which is the same as L of the -L-X functional group, and Z is a fluorophore which generates a fluorescence signal.

Z may be a fluorophore selected from structures displayed by coumarins, cyanine, BODIPY, fluoresceins, rhodamines, pyrenes, carbopyronin, oxazines, xanthenes, thioxanthene, and acridines, or a fluorophore selected from a structure represented by [Chemical Formula 1] or [Chemical Formula 2].

The labeling dye according to the present invention can bind to and label a target biomolecule through the above-described reactive group (X). The reactive group (X) is a functional group capable of reacting with a functional group such as an amino group, an imino group, a thiol group, or a hydroxyl group of a target biomolecule, and may form a covalent bond such as an amide bond, an imide bond, a urethane bond, an ester bond, or a guanidine bond between a labeling dye represented by [Chemical Formula 1] or [Chemical Formula 2] and the target biomolecule.

Furthermore, the reactive group (X) may be bonded to a main skeleton of a labeling dye via a linker (L) to alleviate the steric hindrance between the biomolecule and the labeling dye, and accordingly, it is possible to improve the labeling ratio for a biomolecule such as a nucleic acid, a protein, and a carbohydrate, which has a complex structure.

Further, a labeling dye represented by [Chemical Formula 1] or [Chemical Formula 2] may have a structure further including counter ions. The counter ion is an organic or inorganic anion, and may be appropriately selected in consideration of solubility and stability of the labeling dye, and the like.

Examples of the counter ion of the labeling dye according to the present invention include an inorganic acid anion such as a phosphoric acid hexafluoride ion, a halogen ion, a phosphoric acid ion, a perchloric acid ion, a periodic acid ion, an antimony hexafluoride ion, a tartaric acid hexafluoride ion, a fluoroboric acid ion and a tetrafluoride ion and an organic acid ion such as a thiocyanic acid ion, a benzenesulfonic acid ion, a naphthalenesulfonic acid ion, a p-toluenesulfonic acid ion, an alkylsulfonic acid ion, a benzenecarboxylic acid ion, an alkylcarboxylic acid ion, a trihaloalkylcarboxylic acid ion, an alkylsulfonic acid ion, a trihaloalkylsulfonic acid ion, and a nicotinic acid ion. In addition, a metal compound ion such as bisphenylditol, thiobisphenol chelate and bisdiol-a-diketone, a metal ion such as sodium and potassium, and quaternary ammonium salts may also be selected as the counter ion.

In [Chemical Formula 1] or [Chemical Formula 2], $R_1$ may be selected from the following [Chemical Formula 3] to [Chemical Formula 5], at least one or more of $R_2$ to $R_5$ may be selected from the following [Chemical Formula 3] to [Chemical Formula 5], or at least one or more of $R_6$ and $R_7$ may be selected from the following [Chemical Formula 3] to [Chemical Formula 5].

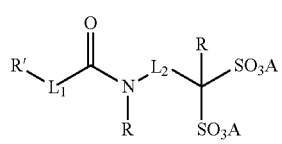

[Chemical Formula 3]

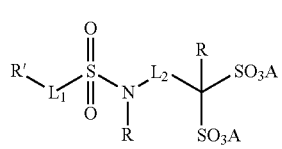

[Chemical Formula 4]

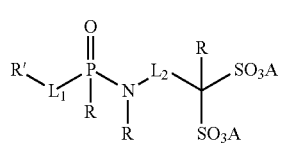

[Chemical Formula 5]

In [Chemical Formula 3] to [Chemical Formula 5], $L_1$ is a linker including 1 to 150 non-hydrogen atoms. In [Chemical Formula 3] and [Chemical Formula 5], $L_1$ is present or not present, and in [Chemical Formula 4], $L_1$ is present.

$L_2$ is a C1-C20 alkylene, or a C1-C20 heteroalkylene including at least one heteroatom. A is hydrogen or $M^+$ ($M^+$ is a counter ion). R is selected from hydrogen, a substituted or unsubstituted C1-C10 alkyl, a substituted or unsubstituted C1-C10 heteroalkyl including at least one heteroatom, a substituted or unsubstituted C2-C10 alkenyl, a substituted or unsubstituted C2-C10 alkynyl, a substituted or unsubstituted C1-C10 alkoxy, and a substituted or unsubstituted C1-C10 haloalkyl, R' represents a site bonded to at least one of $R_1$ to $R_7$, and R' may also be bonded to Q.

Further, in [Chemical Formula 1] or [Chemical Formula 2], at least one or more of R and $R_1$ to $R_7$ may be at least one -L-X functional group. L may be a linker including 1 to 150 non-hydrogen atoms, and X may be a reactive group.

Two or more selected from $R_2$ to $R_5$ may be linked to each other to form a fused ring.

A fused ring may be a substituted or unsubstituted aliphatic fused ring, a substituted or unsubstituted aromatic fused ring, a substituted or unsubstituted aliphatic hetero fused ring including one or more of N, O, and S atoms, a substituted or unsubstituted aromatic hetero fused ring including one or more of N, O, and S atoms, a substituted or unsubstituted fused ring of an aliphatic ring and an aromatic ring, a substituted or unsubstituted fused ring of an aliphatic hetero ring including one or more of N, O, and S atoms and an aromatic hetero ring including one or more of N, O, and S atoms, a substituted or unsubstituted fused ring of a hydrocarbon ring and a hetero ring including one or more of N, O, and S atoms, or a substituted or unsubstituted C60-C84 fullerene.

The fused ring means a cyclic structure in a form where two or more rings share two or more atoms. Examples of the aliphatic fused ring include cyclohexane, cyclopentane, cycloheptane, cyclooctane, cyclohexanedione, and the like, and examples of the aromatic fused ring include naphthalene, anthracene, phenanthryl, triphenylene, fluoranthene, pyrene, perylene, chrysene, acenaphthalene, fluorene, tetracene, or the like.

Further, examples of the aliphatic hetero fused ring including one or more of N, O, and S atoms include piperidine, tetrahydrothiopyran, tetrahydropyran, dioxane, pyrrolidine, tetrahydrofuran, tetrahydrothiophene, and the like, and examples of the aromatic hetero fused ring including one or more of N, O, and S atoms include quinoline, cinnoline, quinazoline, quinoxaline, phthalazine, naphthyridine, phenanthroline, acridine, carbazole, dibenzofuran, benzoimidazole, dibenzothiophene, benzothiophene, benzofuran, benzothiadiazole, pyridopyrimidine, pyridopyrazine, pyrazinopyrazine, isoquinoline, indole, benzoxazole, benzothiazole, benzocarbazole, benzothiazole, phenothiazine, or the like.

In addition, any carbon of the fused ring may be bonded to any one selected from [Chemical Formula 3] to [Chemical Formula 5].

Further, the fused ring may be additionally substituted with one or more substituents as in the following [Chemical Formula 6]. The following [Chemical Formula 6] illustrates a structure in which two or more selected from $R_2$ to $R_5$ of [Chemical Formula 1] are linked to each other to form a fused ring and the substituents $R_{11}$ to $R_{18}$ are included.

[Chemical Formula 6]

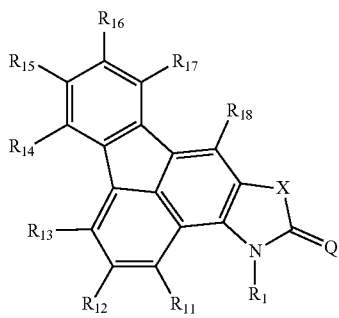

Here, X is selected from CR₆R₇, S, or O, R₁₁ to R₁₈ are the same as the definitions of R₁ to R₅ represented in [Chemical Formula 1] or [Chemical Formula 2], and at least one or more of R₁, R₆, R₇, and R₁₁ to R₁₈ may be one selected from [Chemical Formula 3] to [Chemical Formula 5]. The definitions of [Chemical Formula 3] to [Chemical Formula 5] are the same as those described above.

In addition, in [Chemical Formula 6], adjacent substituents may form a cycloalkyl, a cycloalkenyl, an aromatic ring, an aliphatic hetero ring including one or more of N, O, and S atoms, or an aromatic hetero ring including one or more of N, O, and S atoms, and the substituent in the same carbon may form a spiro bond, a carbonyl group, a substituted or unsubstituted imine group, or a substituted or unsubstituted alkenyl group.

Specific examples of the labeling dye represented by [Chemical Formula 1] or [Chemical Formula 2] according to the present invention are as follows.

[Compound 1]

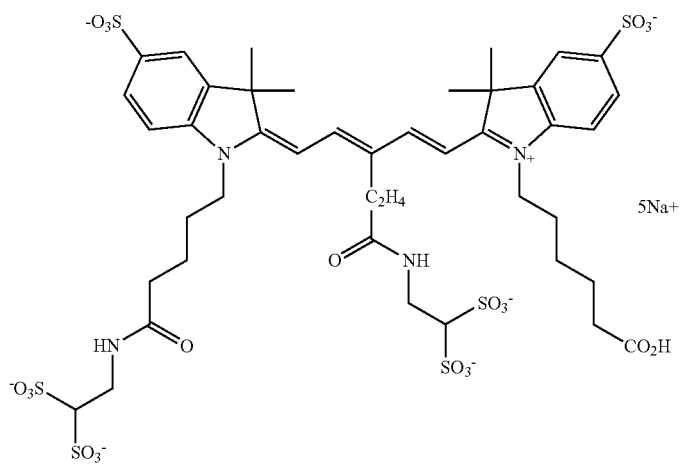

[Compound 2]

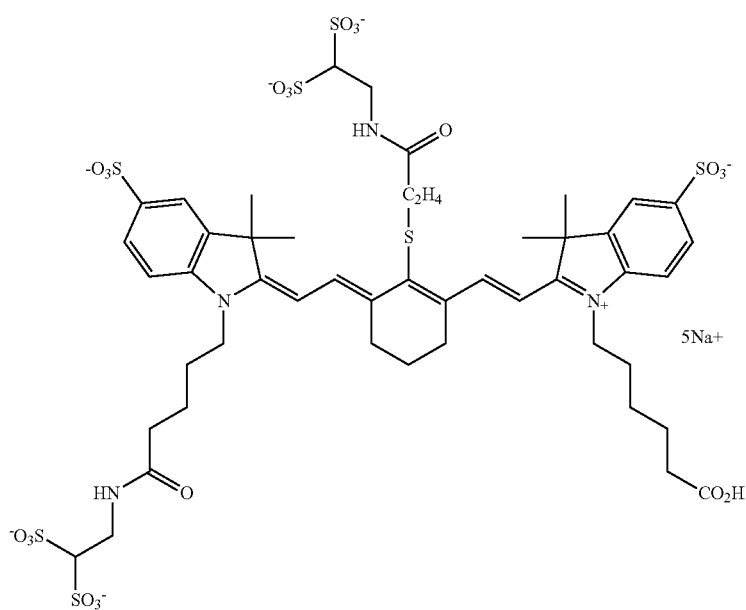

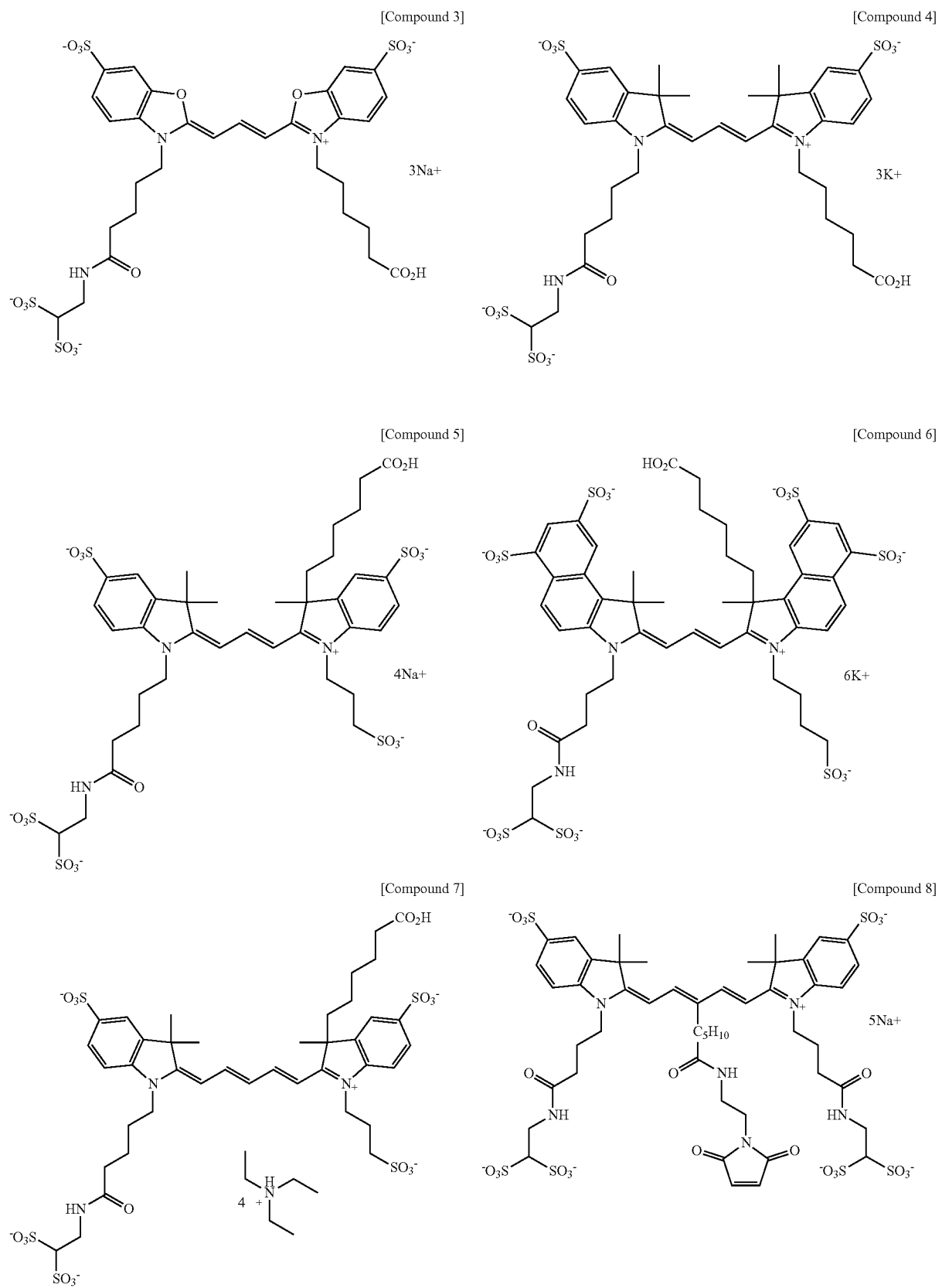

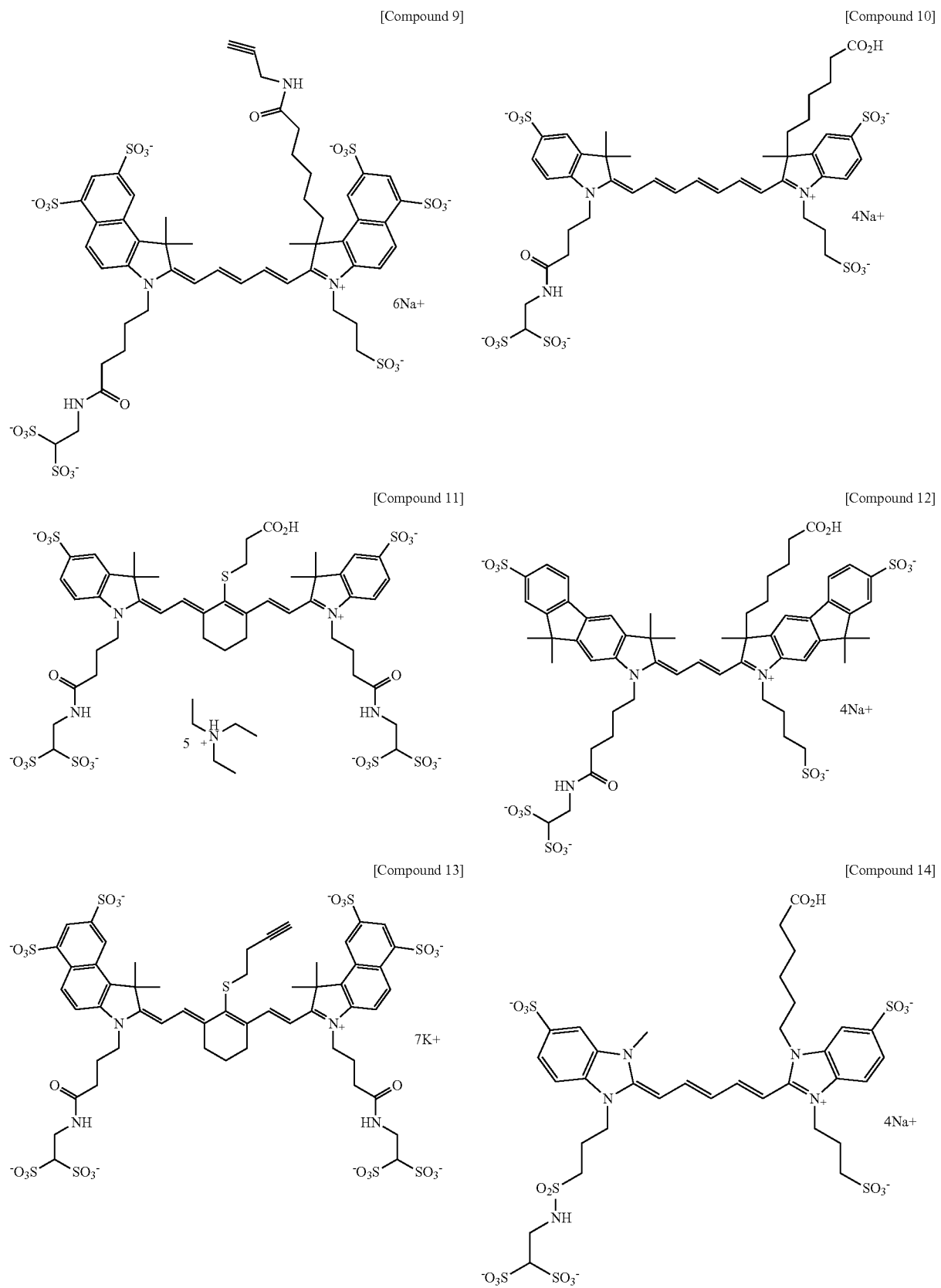

[Compound 15]
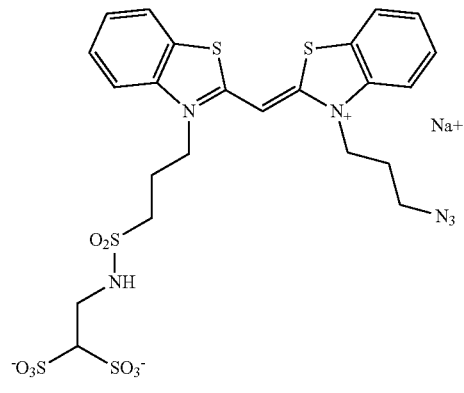
[Compound 16]
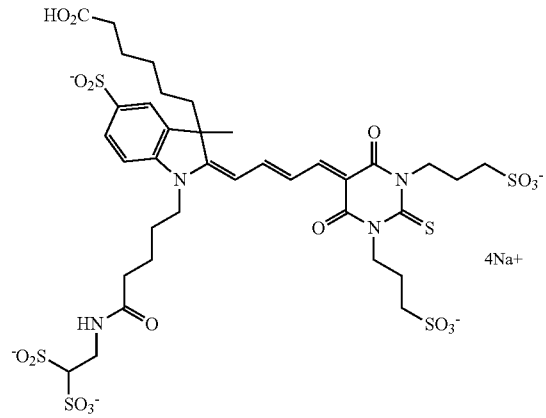
[Compound 17]
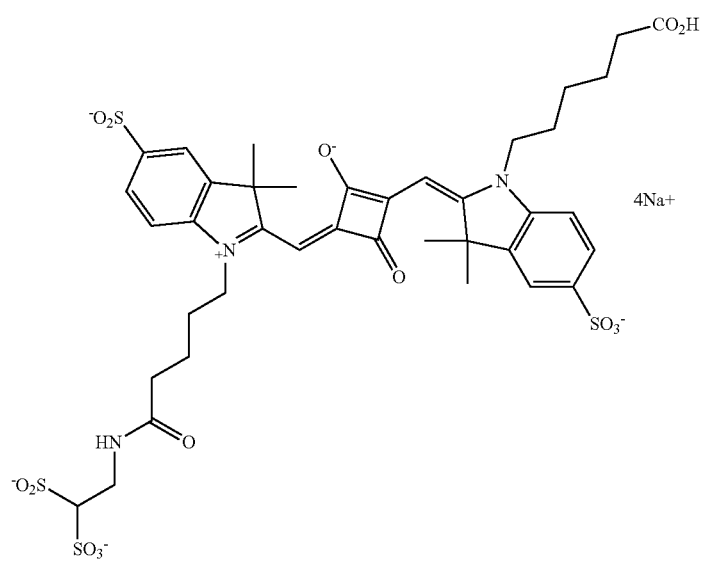
[Compound 18]
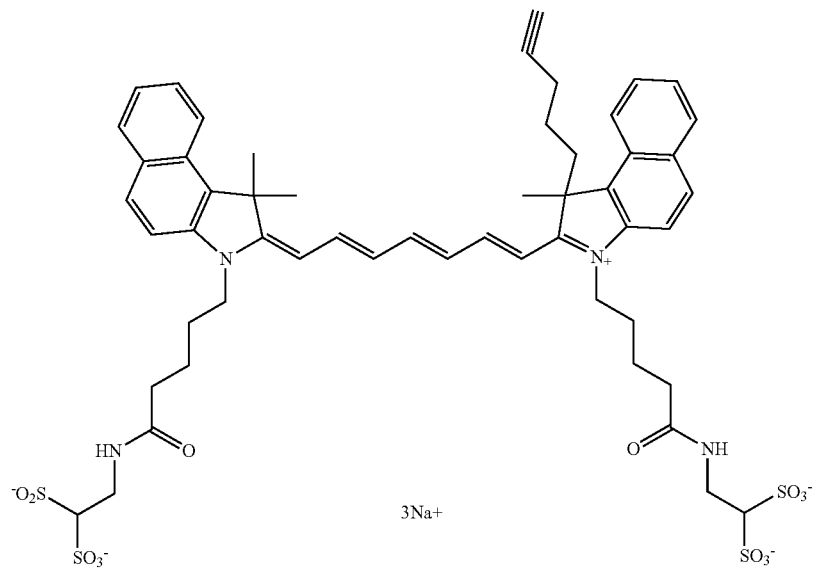

[Compound 19]
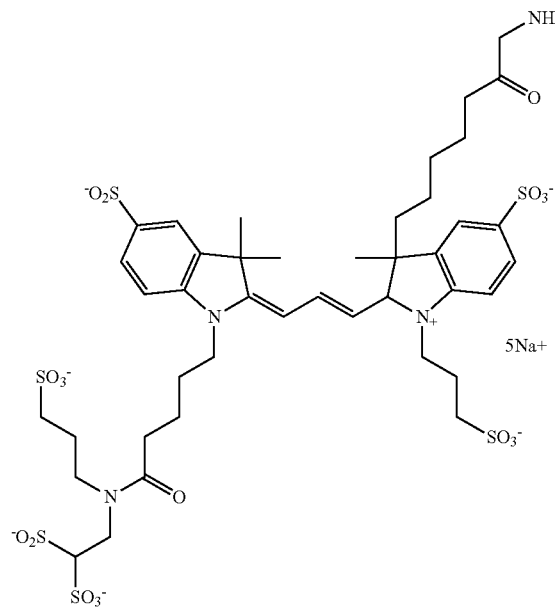
[Compound 20]
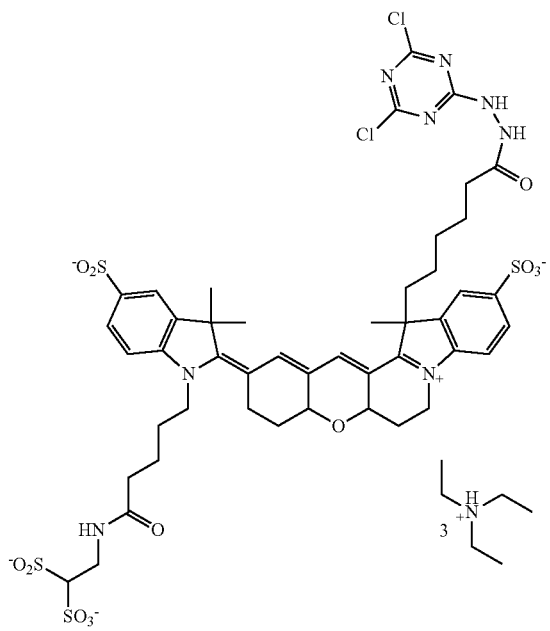
[Compound 21]
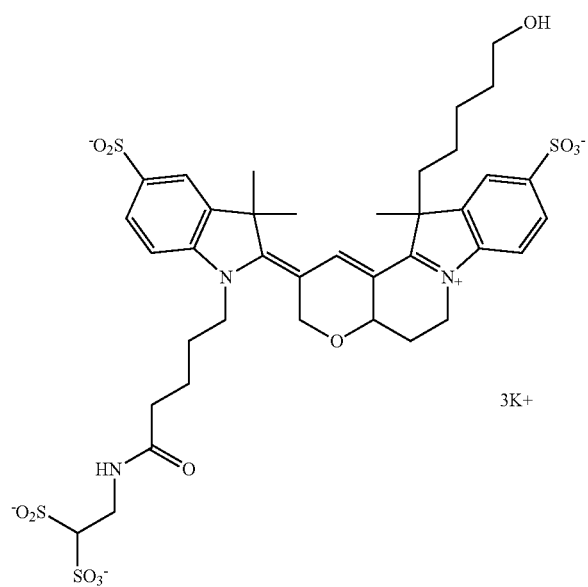
[Compound 22]
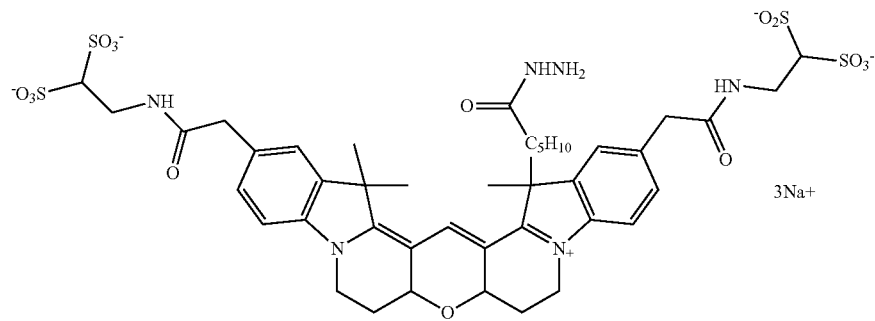

[Compound 23]
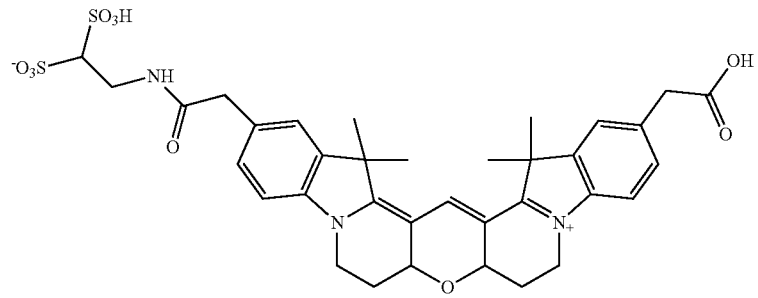
[Compound 24]
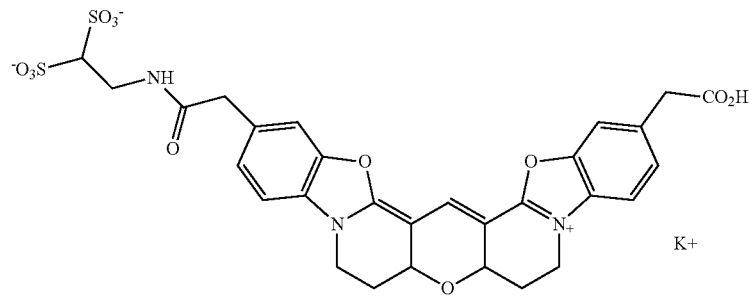
K+
[Compound 25]
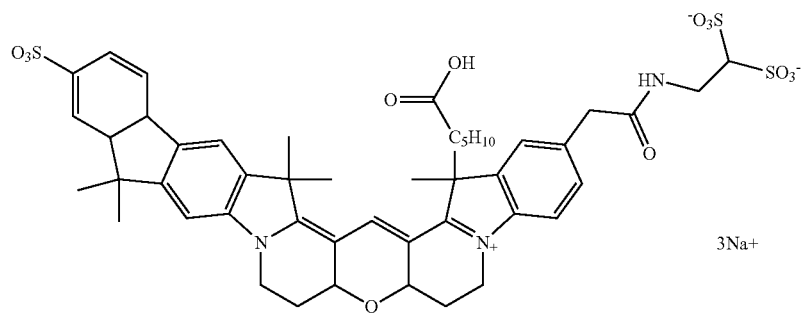
3Na+
[Compound 26]
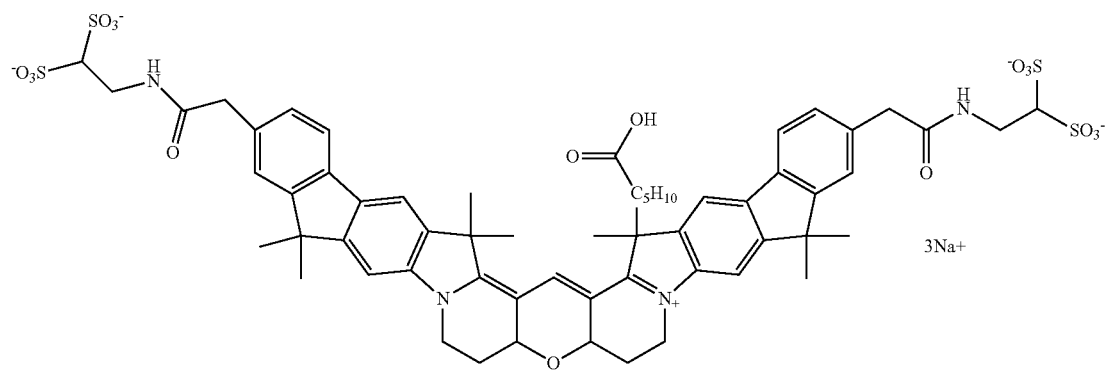
3Na+
[Compound 27]
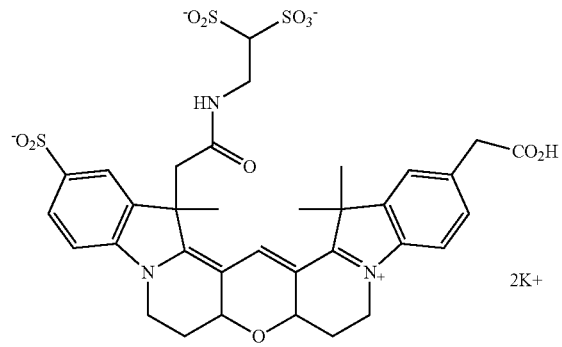
2K+

[Compound 28]
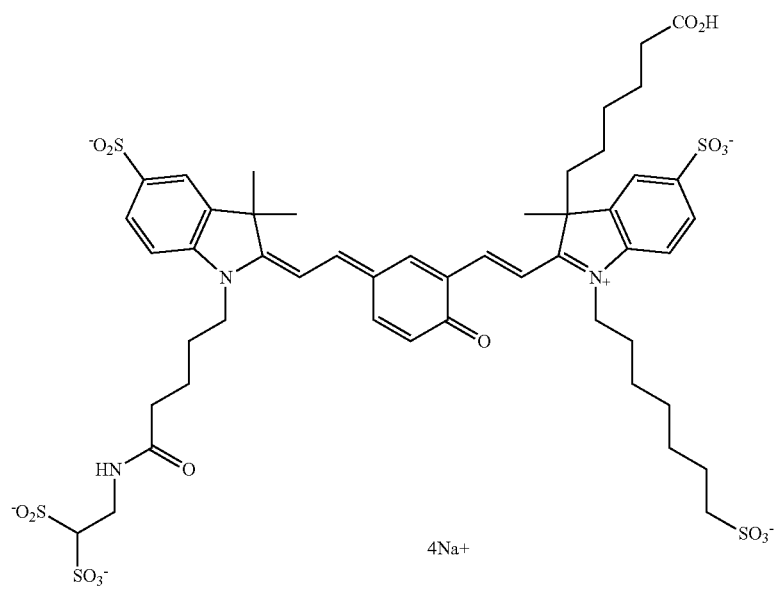
4Na+
[Compound 29]
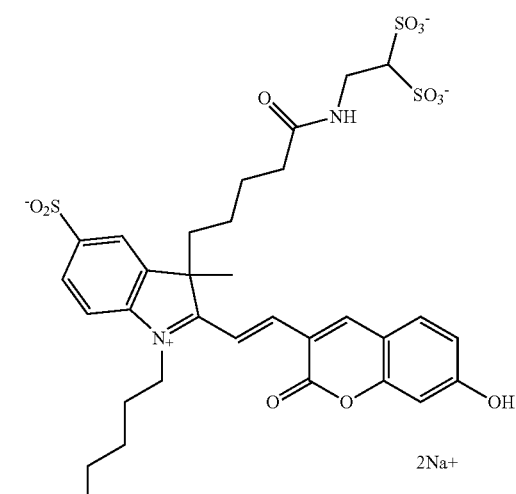
2Na+
[Compound 30]
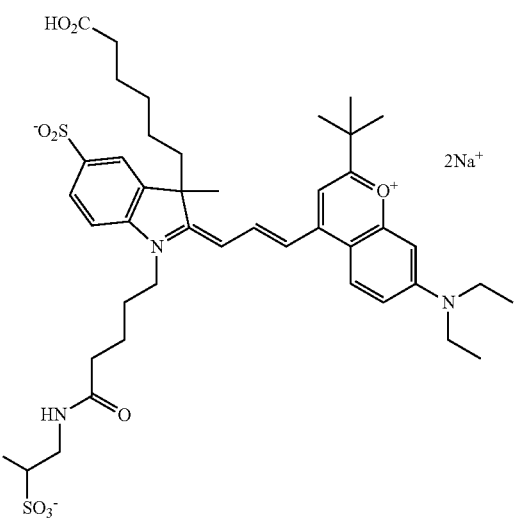
2Na+
[Compound 31]
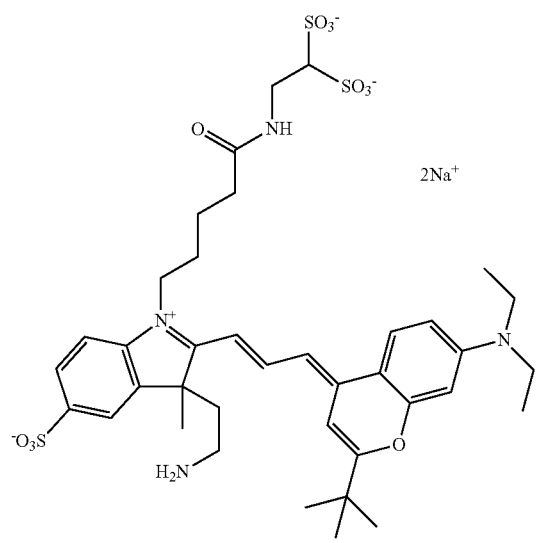
2Na+
[Compound 32]
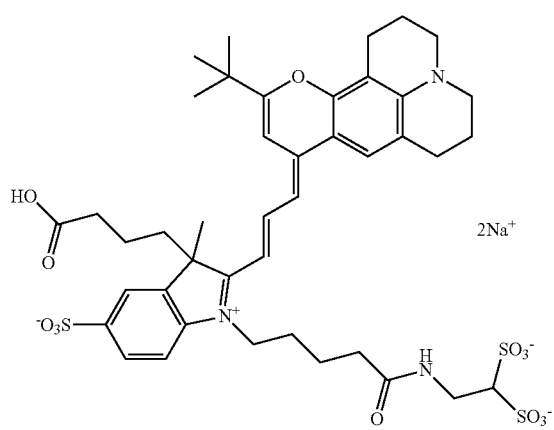
2Na+

[Compound 33]
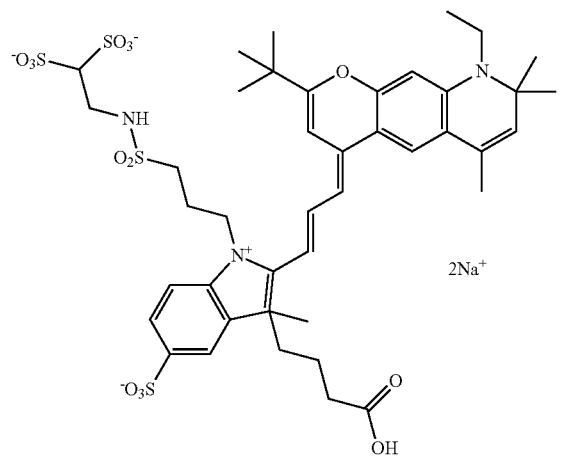
[Compound 34]
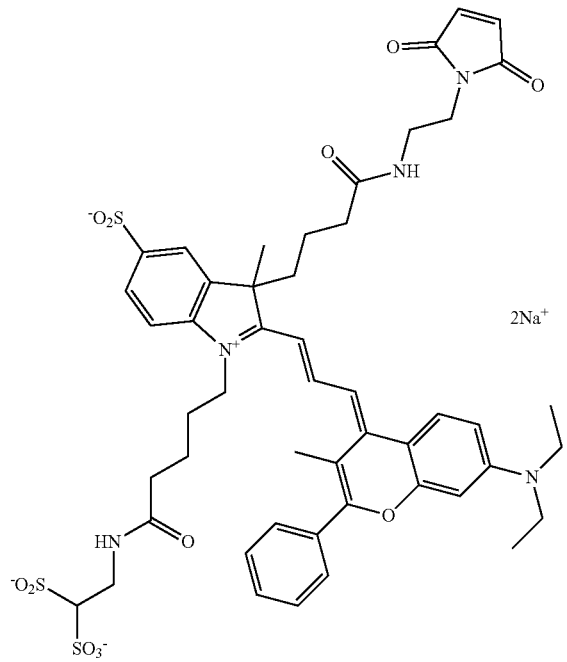
[Compound 35]
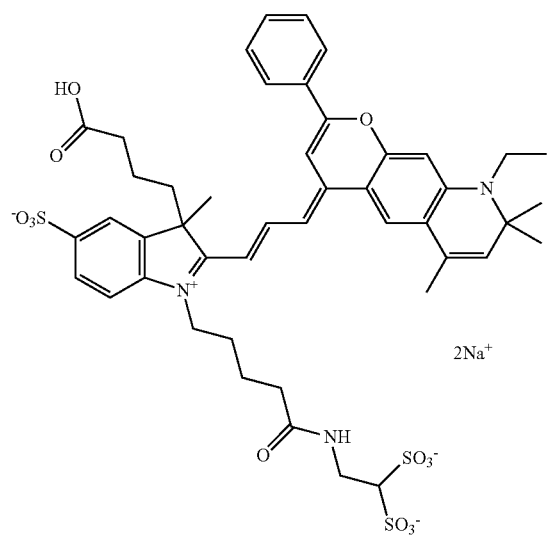
[Compound 36]
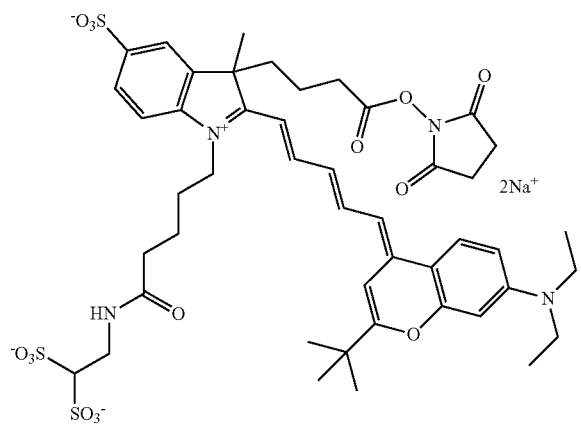

[Compound 37]
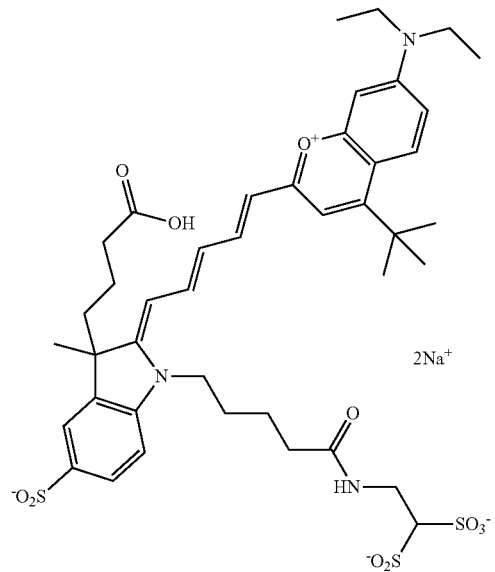
[Compound 38]
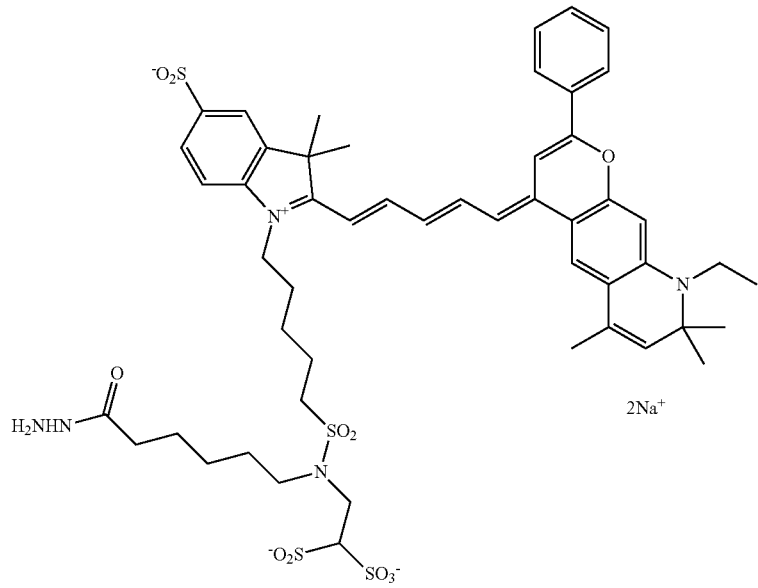

-continued
[Compound 39]
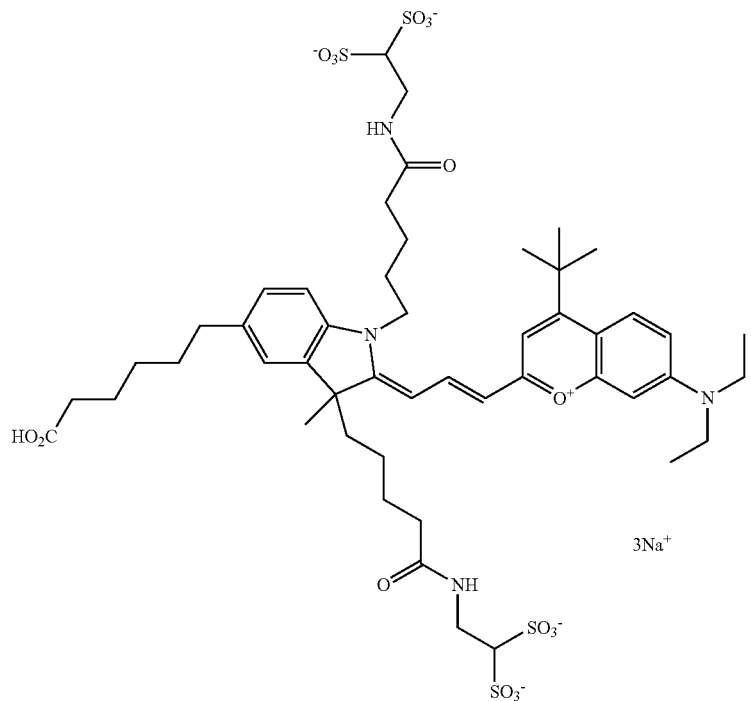
[Compound 40]
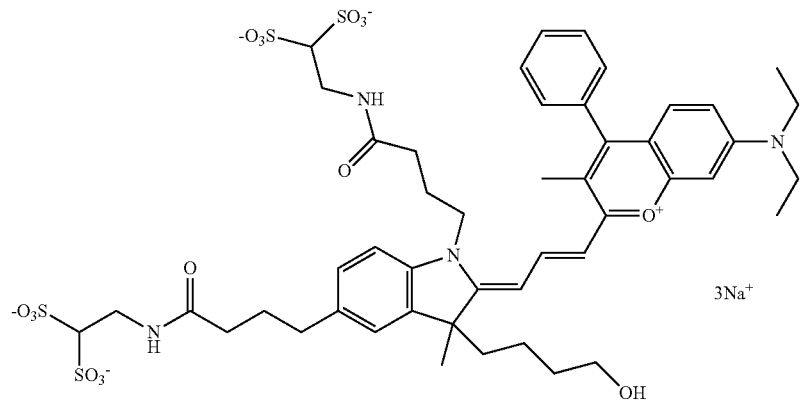
[Compound 41]
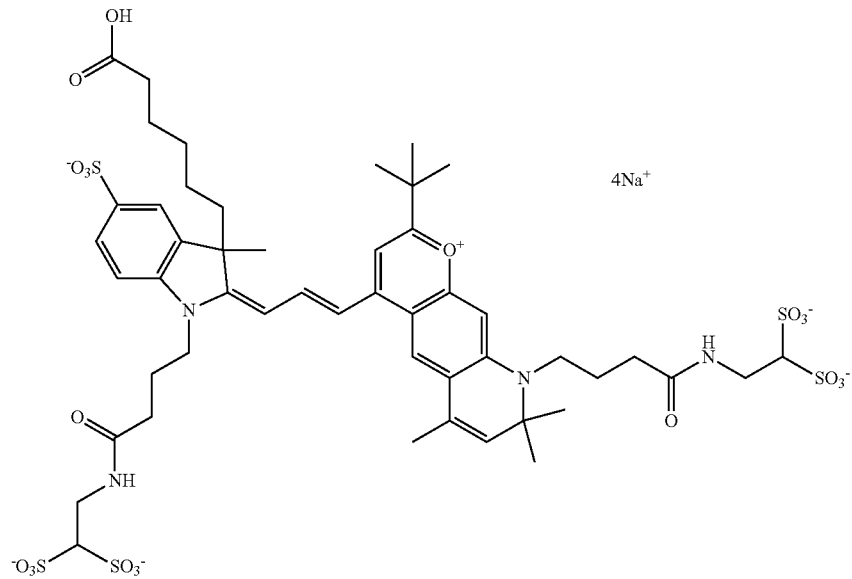

[Compound 42]
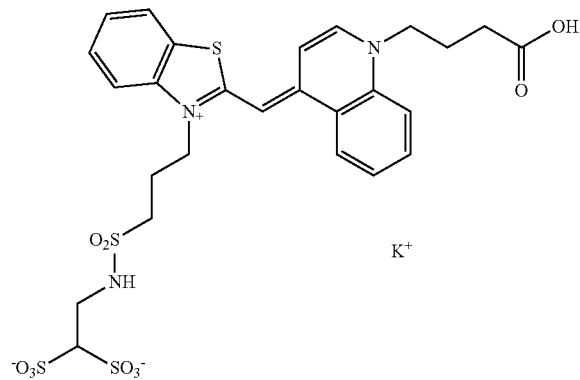
[Compound 43]
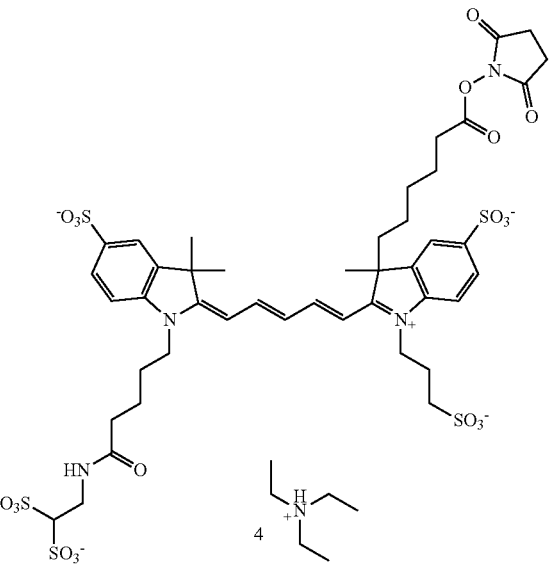
[Compound 44]
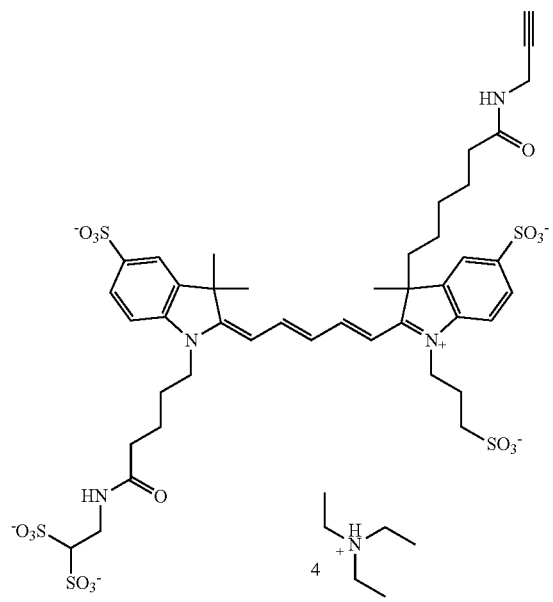
[Compound 45]
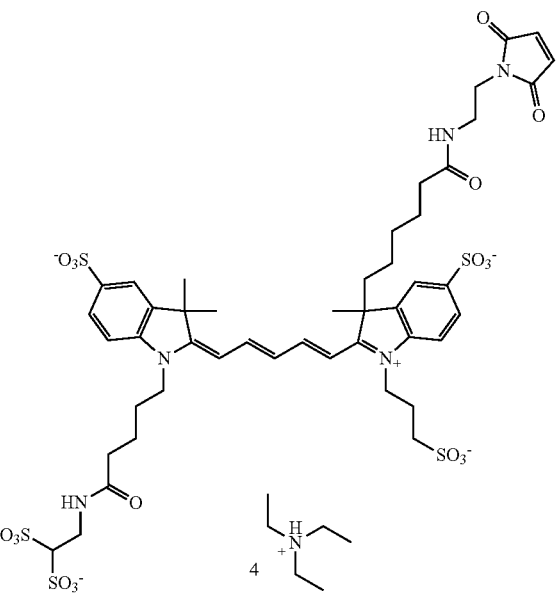
[Compound 46]
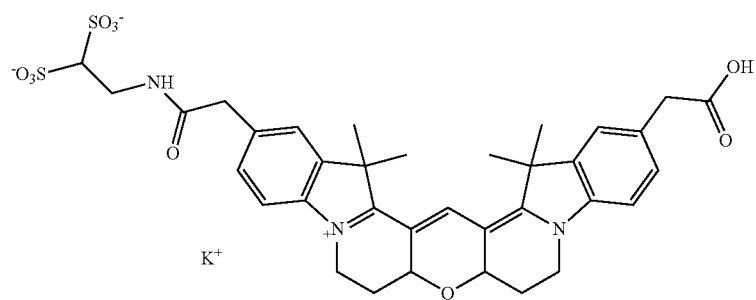

-continued
[Compound 47]
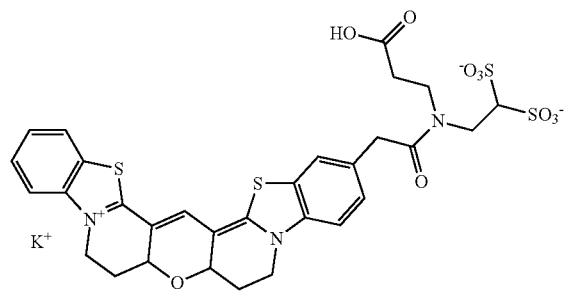
[Compound 48]
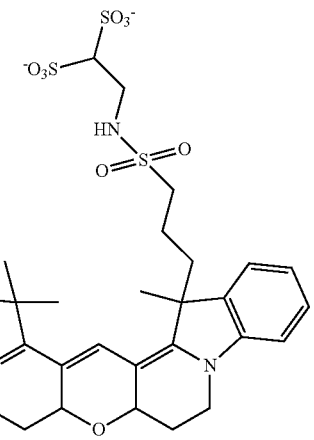
[Compound 49]
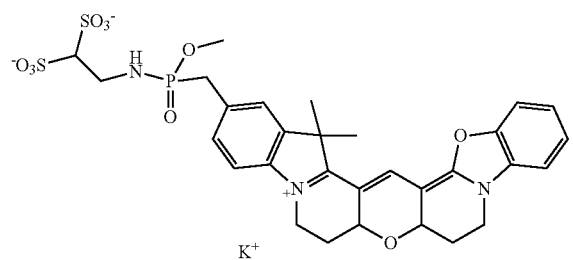
[Compound 50]
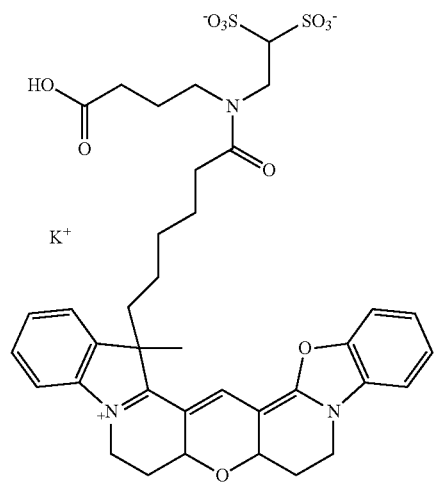
[Compound 51]
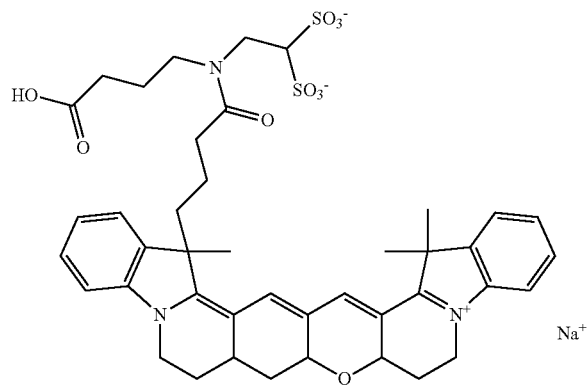
[Compound 52]
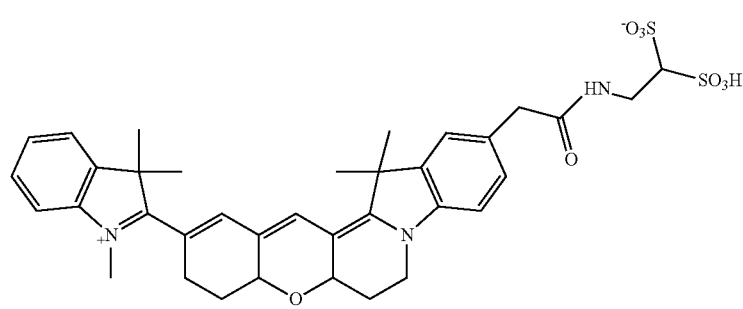

-continued

[Compound 53]

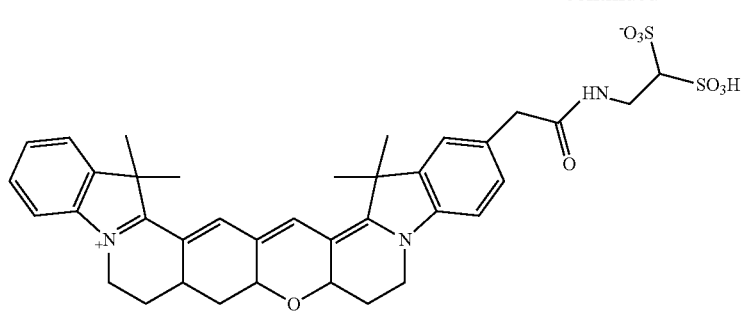

The labeling dye represented by [Chemical Formula 1] or [Chemical Formula 2] according to the present invention may bind to a biomolecule to exhibit a fluorescence signal.

The biomolecule may be at least one selected from antibodies, lipids, proteins, peptides, carbohydrates, and nucleic acids (including nucleotides).

Specific examples of the lipids include fatty acids, phospholipids, lipopolysaccharides, and the like, and specific examples of the carbohydrates include monosaccharides, disaccharides, and polysaccharides (for example, dextran).

The biomolecule is a functional group for reacting with any functional group of a labeling dye represented by [Chemical Formula 1] or [Chemical Formula 2] or with a reactive group bonded to the labeling dye, and may include at least one selected from amino, sulfhydryl, carbonyl, hydroxyl, carboxyl, phosphate, and thiophosphate or have a derivative form thereof.

Further, the biomolecule may be an oxy or dioxy polynucleic acid which includes at least one selected from amino, sulfhydryl, carbonyl, hydroxyl, carboxyl, phosphate, and thiophosphate or have a derivative form thereof.

Furthermore, the labeling dye represented by [Chemical Formula 1] or [Chemical Formula 2] of the present invention may be used to label a drug, a hormone (including a receptor ligand), a water-soluble vitamin, a fat-soluble vitamin, a mineral, a receptor, an enzyme or enzyme substrate, a cell, a cell membrane, a toxin, a microorganism, a nanobio material(polystyrene microsphere, and the like), or the like, which includes at least one selected from amino, sulfhydryl, carbonyl, hydroxyl, carboxyl, phosphate, and thiophosphate, in addition to the above-described biomolecule.

Here, the water-soluble vitamin may include a Vitamin B group, Vitamin C, pantothenic acid, niacin, folic acid, biotin, inositol, and the like, and the fat-soluble vitamin may include Vitamin A, Vitamin E, Vitamin D, Vitamin K, and the like. Further, the mineral may include acid calcium, calcium phosphate monobasic, potassium phosphate dibasic, potassium chloride, magnesium phosphate dibasic, sodium hydrogen carbonate, zinc oxide, ferric pyrophosphate, manganese sulfate, potassium iodide, and the like, but is not limited thereto.

In addition, the present invention provides a labeling kit including the labeling dye. The labeling kit may further include an enzyme for a reaction with a target molecule, a solvent (buffer, and the like), other reagents, and the like, if necessary. As the solvent, it is possible to use a buffer selected from the group consisting of a phosphate buffer, a carbonate buffer, and a Tris buffer, an organic solvent selected from dimethyl sulfoxide, dimethylformamide, dichloromethane, methanol, ethanol, and acetonitrile, water, or the like, and solubility can be adjusted by introducing various functional groups into a labeling dye according to the type of solvent.

Method for Labeling Biomolecule Using Labeling Dye

As a method for labeling a biomolecule with the labeling dye represented by [Chemical Formula 1] or [Chemical Formula 2] of the present invention, a labeling method for measuring fluorescence of a solid or semi-solid state biomolecule may be applied to the labeling of all possible biomolecules.

A labeling method which is highly sensitive, chemically stable and excellent in operability may be provided using the labeling dye represented by [Chemical Formula 1] or [Chemical Formula 2] instead of a fluorescent dye in the related art.

DNA Microarray Method

In a DNA microarray method, a labeling dye is reacted with a target nucleic acid to be labeled (that is, the dye is allowed to intercalate in the target nucleic acid) to label the target nucleic acid, and in this case, a fluorescence signal may be generated by preparing a single-stranded probe nucleic acid having a base sequence complementary to the target nucleic acid, hybridizing the target nucleic acid denatured into single strands and the probe nucleic acid on a substrate, and then allowing the fluorescent dye to intercalate in the target nucleic acid.

As the probe nucleic acid immobilized on a substrate in this labeling method, it is possible to use a probe nucleic acid prepared by amplifying a library of cDNA such as cDNA, a library of a genome, or all genomes as a template with a PCR method, when the expression of a gene is examined.

Further, it is possible to use a probe nucleic acid by which various oligonucleotides corresponding to a mutation based on the standard sequence as already known are synthesized, when a mutation of a gene and the like are examined.

As the immobilization of the probe nucleic acid on the substrate, an appropriate method may be selected depending on the type of nucleic acid or the type of substrate. For example, it is also possible to use a method of performing electrostatic bonding to a substrate surface-treated with a cation such as polylysine using a charge of a DNA.

PCR Method

In a PCR method, fluorescence of a target nucleic acid is measured by labeling a probe complementary to a base sequence of the target nucleic acid to be labeled with a dye, reacting the probe with the target nucleic acid before or after amplifying the target nucleic acid.

Specifically, an elongation reaction of the target nucleic acid is performed by an enzyme (a DNA polymerase, an RNA polymerase), and in this case, the enzyme recognizes a double-stranded nucleic acid sequence formed by a primer consisting of the target nucleic acid and the oligonucleotide, and the elongation reaction is performed from the recognized position, and only a desired gene region is amplified.

When the enzyme synthesizes a nucleic acid, a synthesis reaction is performed using nucleotides (dNTP, NTP) as raw materials.

In this case, when a nucleotide having a dye is mixed with a typical nucleotide (dNTP, NTP) at an arbitrary ratio, a nucleic acid into which the dye having the ratio is introduced may be synthesized. Further, a nucleic acid into which a labeling dye is introduced may also be synthesized by introducing a nucleotide having an amino group at an arbitrary ratio by PCR, and then bonding the labeling dye to the nucleotide.

When the enzyme synthesizes a nucleic acid, a synthesis reaction is performed using nucleotides as raw materials, and when a product obtained by replacing a 3' OH of the nucleotide with H in this case is used, the extension reaction of the nucleic acid is no longer performed, and the reaction is terminated at the time point. This nucleotide, dideoxynucleotide triphosphate (ddNTP), is called a terminator. When a nucleic acid is synthesized by mixing a terminator with a typical nucleotide, the terminator is introduced at a certain probability and the reaction is terminated, so that nucleic acids with various lengths are synthesized.

When these are subjected to size separation by gel electrophoresis, DNAs are arranged in order of length. Here, when the terminator is labeled with a different labeling dye for each type of base, a tendency depending on each base is observed at the end point (3' end) of the synthesis reaction, so that the base sequence information of the target nucleic acid may be obtained by reading fluorescence information beginning with the labeling dye labeled to the terminator. Further, the nucleic acid may be hybridized to the target nucleic acid using a primer that has been labeled with a labeling dye in advance, instead of a terminator. In addition, a peptide nucleic acid (PNA) may also be used as a probe. The PNA is a nucleic acid in which a pentose-phosphate skeleton, which is the basic skeleton structure of a nucleic acid, has been substituted with a polyamide skeleton including glycine as a unit, and thus has a three-dimensional structure very similar to that of a nucleic acid, and binds very specifically and strongly to a nucleic acid having a complementary base sequence. Accordingly, the PNA may be used for not only existing DNA analysis methods such as in-situ hybridization method, but also as a reagent for telomere research by applying the PNA to a telomere PNA probe.

For example, the detection may be carried out by contacting a double-stranded DNA with a PNA having base sequence(s) complementary to all or a part of the base sequence of DNA and having been labeled with a labeling dye for hybridization, heating the mixture to form single-stranded DNA, cooling the mixture slowly to room temperature to prepare a PNA-DNA complex, and measuring the fluorescence thereof.

In the aforementioned example, a method for measuring fluorescence of a product by amplifying the target nucleic acid by the PCR method has been described, but in this method, the amount of the amplified product needs to be examined by confirming the size of the product by electrophoresis and then measuring fluorescence intensity. For this purpose, the amount of the product may also be measured in real time using a probe which is designed to generate fluorescence by utilizing energy transfer of the fluorescence dye and hybridizing the target nucleic acid with the product of the PCR method. For example, DNA labeled with a donor and an acceptor may be used. Examples of a specific labeling method include a molecular beacon method of confirming the presence of a nucleic acid having a specific sequence, a TaqMan-PCR method, a cycling probe method, and the like.

Other Labeling Methods

Further, an intracellular signaling phenomenon may also be observed using the labeling dye of the present invention. Various enzymes and the like are involved in internal signaling or a reaction of a cell associated therewith. It is known that in a representative signaling phenomenon, a special protein kinase is activated, and accordingly, protein phosphorylation is induced, and as a result, signaling is initiated. The binding and hydrolysis of nucleotides (for example, ATP or ADP) play a crucial role in their activity, and an intracellular signaling phenomenon may be observed with high sensitivity by introducing a labeling dye into a nucleotide derivative.

Further, the labeling dye of the present invention may also be used for observing gene expression phenomena using RNA interference (RNAi). RNAi suppresses the expression of a target gene by introducing double-stranded RNA (dsRNA) into cells to degrade the mRNA of the target gene, and the RNAi phenomenon can be observed by labeling the designed dsRNA with a labeling dye.

Hereinafter, the present invention will be described in more detail through a method for synthesizing a specific labeling dye and the Examples and the Comparative Experiments according to the present invention.

PREPARATION EXAMPLES

1) Preparation of [Compound 7]

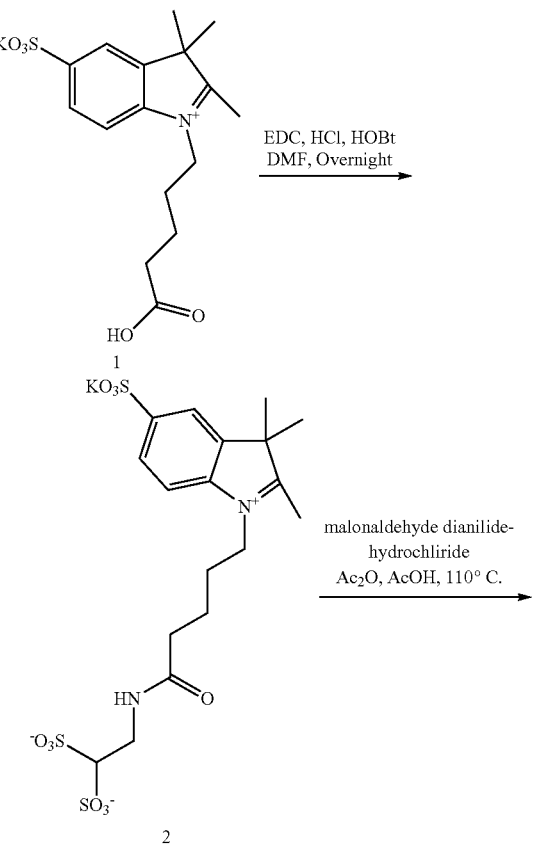

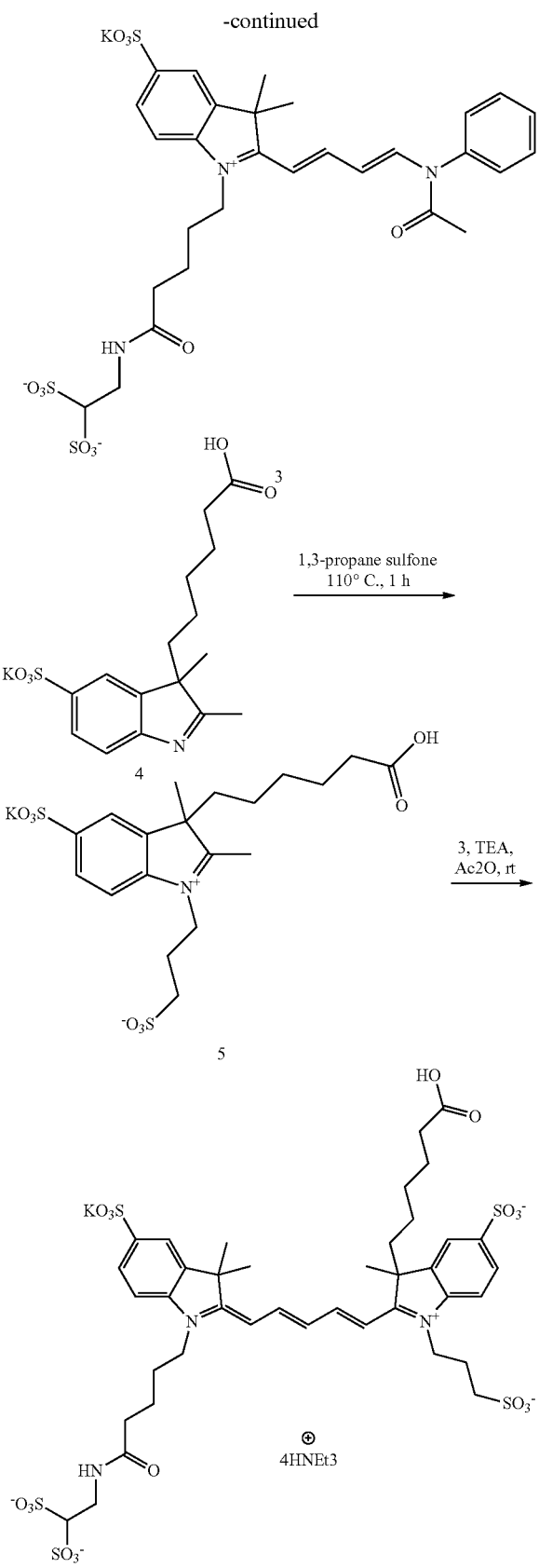

g of 1-(3-dimethylaminopropyl)-3-ethylcarbodiimide hydrochloride (EDC hydrochloride), and 5.6 g of 1-hydroxybenzotriazole (HOBt) were introduced into 77 ml of dimethylformamide (DMF), and the resulting mixture was stirred at room temperature for 24 hours. Thereafter, the product was concentrated under reduced pressure and a solid was precipitated with ethylene acetate. The precipitated solid was filtered and vacuum dried to prepare Intermediate 2 (4.0 g, 21.6%).

Intermediate 2 (4.0 g) and 1.9 g of malonaldehyde dianilide hydrochloride were introduced into a reactor, and 20 ml of each of acetic acid and acetic anhydride were added thereto, and then the resulting mixture was refluxed at 110° C. and stirred for 6 hours. Thereafter, after cooling, the product was concentrated under reduced pressure, and a solid was precipitated with ethyl acetate. The precipitated solid was filtered and vacuum dried to prepare Intermediate 3 (4.6 g, 87.1%).

Intermediate 3 (3.6 g), 2.5 g of Intermediate 5 (U.S. Pat. No. 7,927,830 B2), 10.8 ml of triethylamine, and 10.8 ml of acetic anhydride were introduced into a reactor, and the resulting mixture was stirred at 60° C. for 6 hours. The product was cooled to room temperature, and then added dropwise to ethyl acetate. The precipitated solid was filtered, and then purified with MPLC to prepare Compound 7 (640 mg, 9.01%).

2) Preparation of [Compound 4]

7.7 g of ammonium 2-aminoethane-1,1-disulfonic acid hydrate, 12.1 g of Intermediate 1 (WO 2003/074091 A2), 8.0

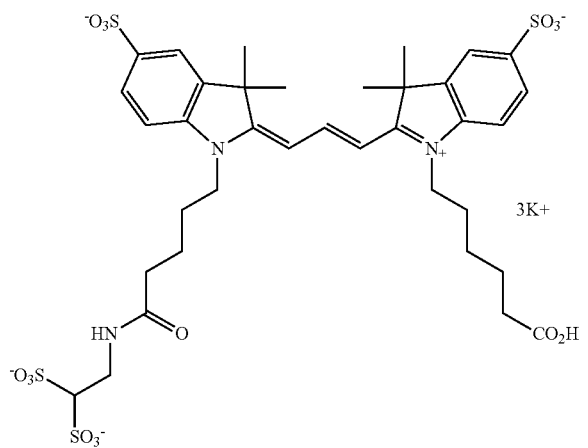

Intermediates 6 and 7 (WO 2012/027623 A2) prepared in the same manner as in the method of preparing Intermediate 2 were used and reacted, and Compound 4 (WO 2012/027623 A2) (121 mg, 11.9%) was prepared using reverse phase chromatography and an ion exchange resin.

3) Preparation of [Compound 3]

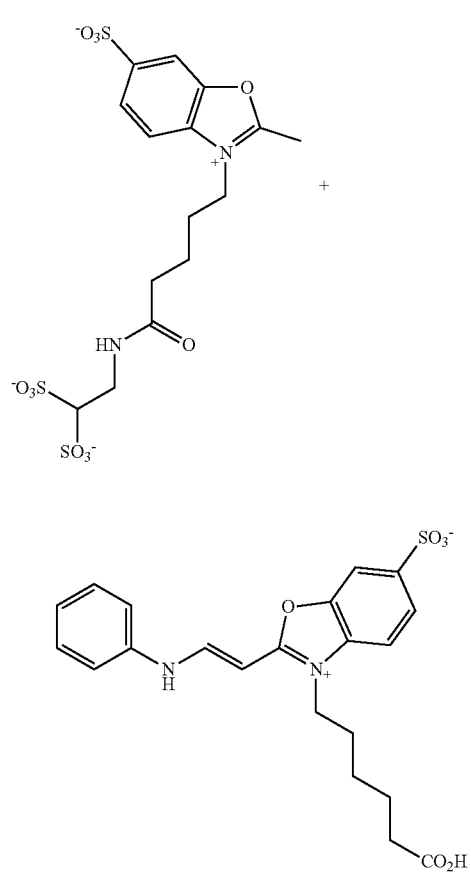

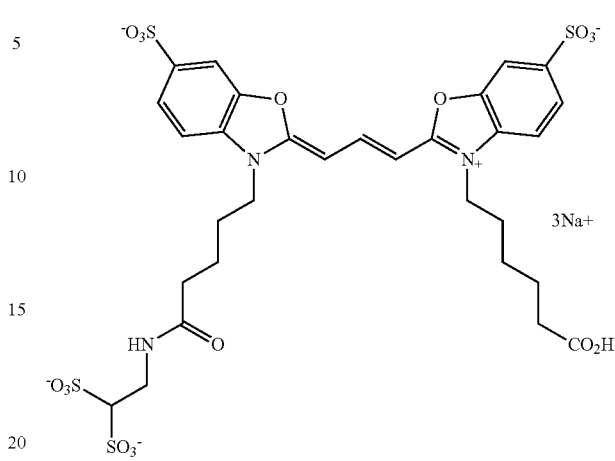

Compound 3 (154 mg, 15.4%) was prepared using 2-methyl-1,3-benzoxazole-6-sulfonic acid as a raw material instead of 2,3,3-trimethylindole-5-sulfonic acid in the method of preparing Compound 4.

4) Preparation of [Compound 23]

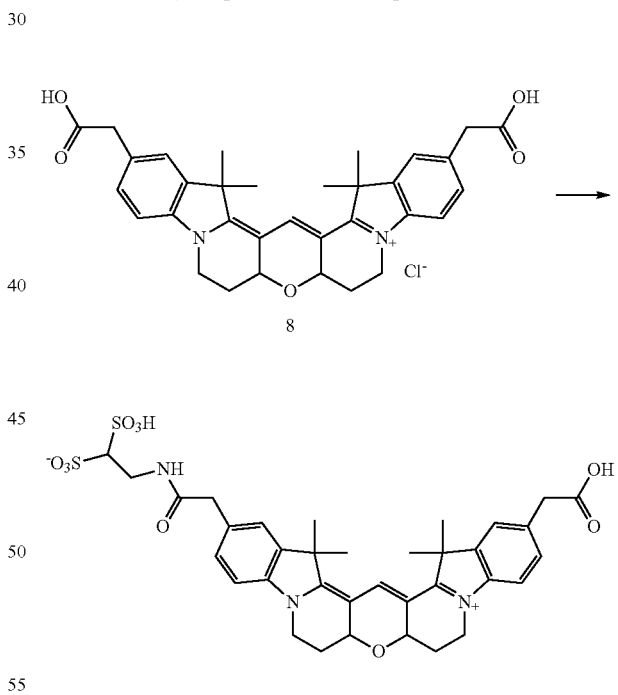

268 mg of Intermediate 8 (US2003-0224391), 200 mg of ammonium 2-aminoethane-1,1-disulfonic acid hydrate, 108 mg of 1-(3-dimethylaminopropyl)-3-ethylcarbodiimide hydrochloride (EDC hydrochloride), and 76 mg of 1-hydroxybenzotriazole (HOBt) were introduced into 10 ml of dimethylformamide (DMF), and the resulting mixture was stirred at room temperature for 12 hours. Thereafter, the product was concentrated under reduced pressure and a solid was precipitated with ethylene acetate. The precipitated solid was subjected to reverse phase chromatography to prepare Compound 23 (110 mg, 32.4%).

5) Preparation of [Compound 30]

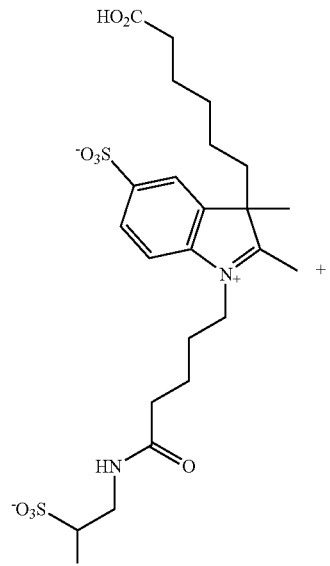

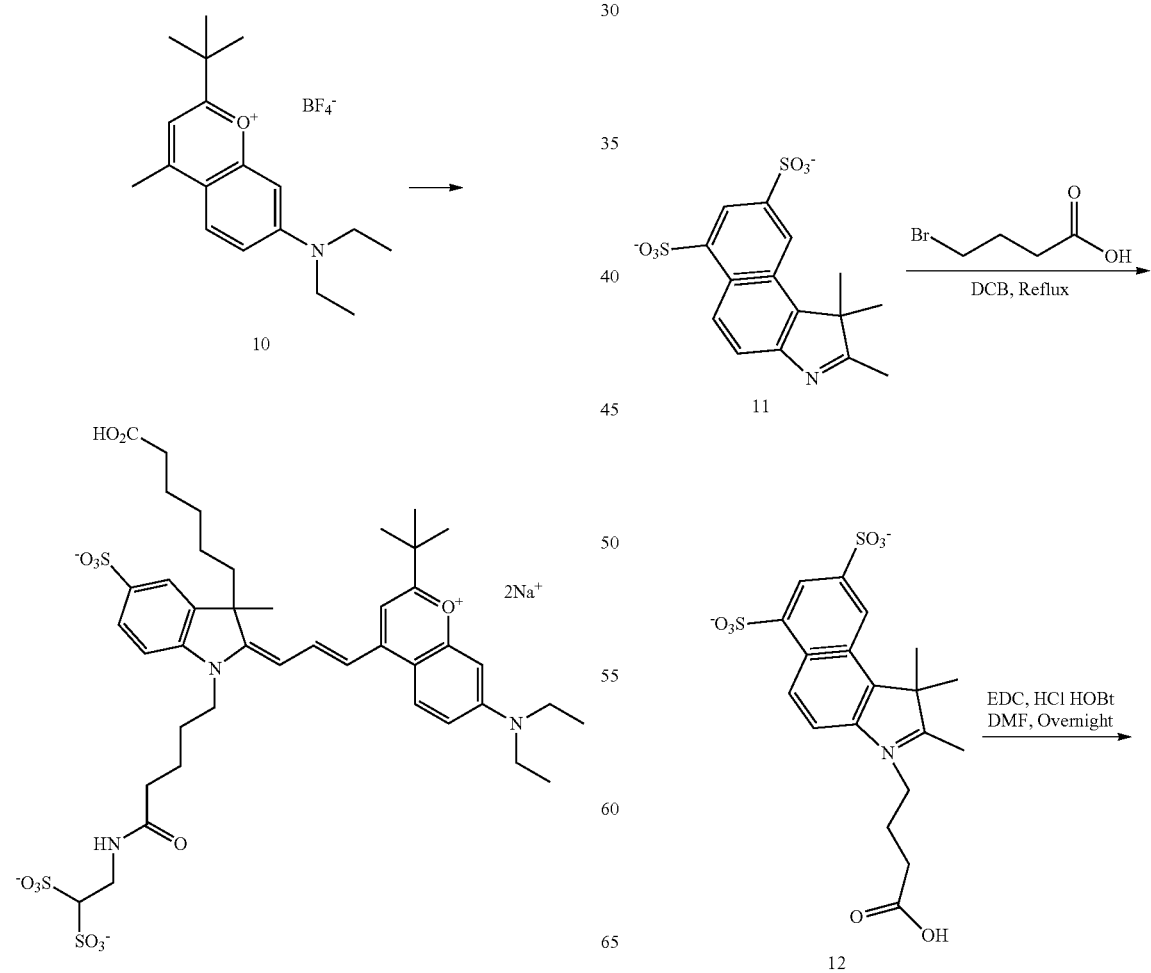

Intermediates 9 and 10 (Journal of the American Chemical Society, 137(14), 4759-4765; 2015) prepared using 6-(2,3-dimethyl-5-sulfo-3H-indol-3-yl)hexanoic acid as a raw material instead of 2,3,3-trimethylindole-5-sulfonic acid in the method of preparing Intermediate 2 were used and reacted (WO 2014/035712 A1), and Compound 30 (57 mg, 9.3%) was prepared using reverse phase chromatography and an ion exchange resin.

6) Preparation of [Compound 5]

Compound 5 (308 mg, 16.2%) was prepared in the same manner as in the method of preparing Compound 7, except that N,N-diphenylformamidine was used instead of malonaldehyde dianilide hydrochloride.

7) Preparation of [Compound 10]

Compound 10 (57 mg, 9.7%) was prepared in the same manner as in the method of preparing Compound 7, except that glutaconaldehydedianil hydrochloride was used instead of malonaldehyde dianilide hydrochloride.

8) Preparation of [Compound 6]

-continued

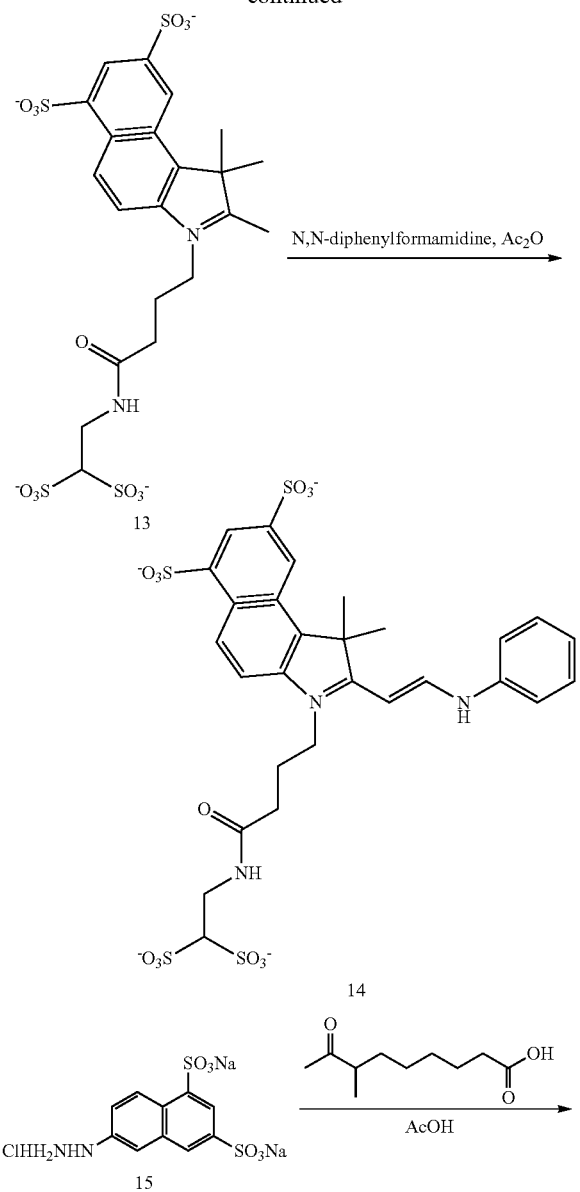

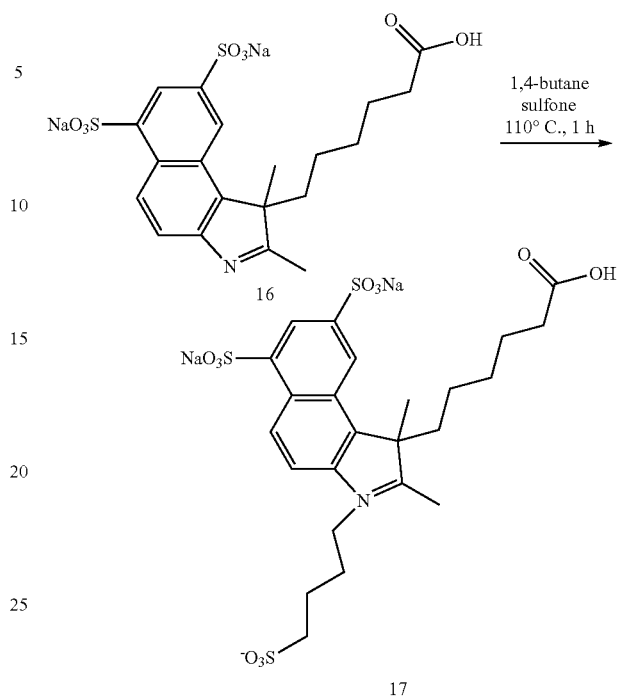

Intermediates 11 and 16 were prepared and used by referencing Chem. Eur. J. 2017, 23, 3966-3978, and Compound 6 (105 mg, 8.3%) was prepared in the same manner as in the method of preparing Compound 7, except that N,N-diphenylformamidine was used instead of malonaldehyde dianilide hydrochloride, 1,4-butane sultone was used instead of 1,3-propane sultone, and an ion exchange resin was used.

9) Preparation of [Compound 18]

Compound 18 (200 mg, 9.7%) was synthesized in the same manner as in WO 2003/074091 using 1,1,2-trimethyl benzo[e]indole hydrochloride and the method of preparing Compound 7.

10) Preparation of [Compound 11]

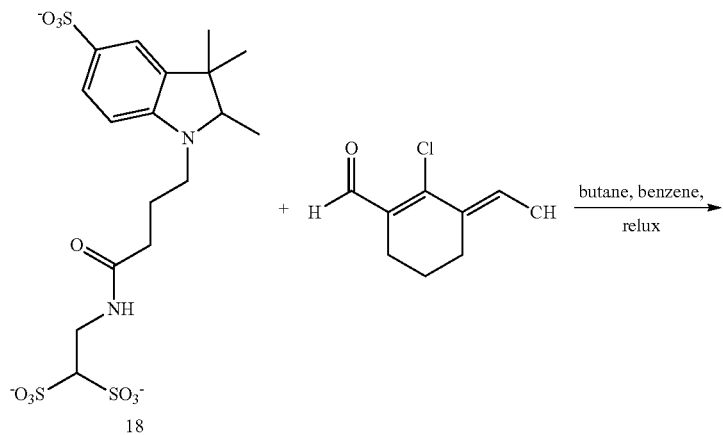

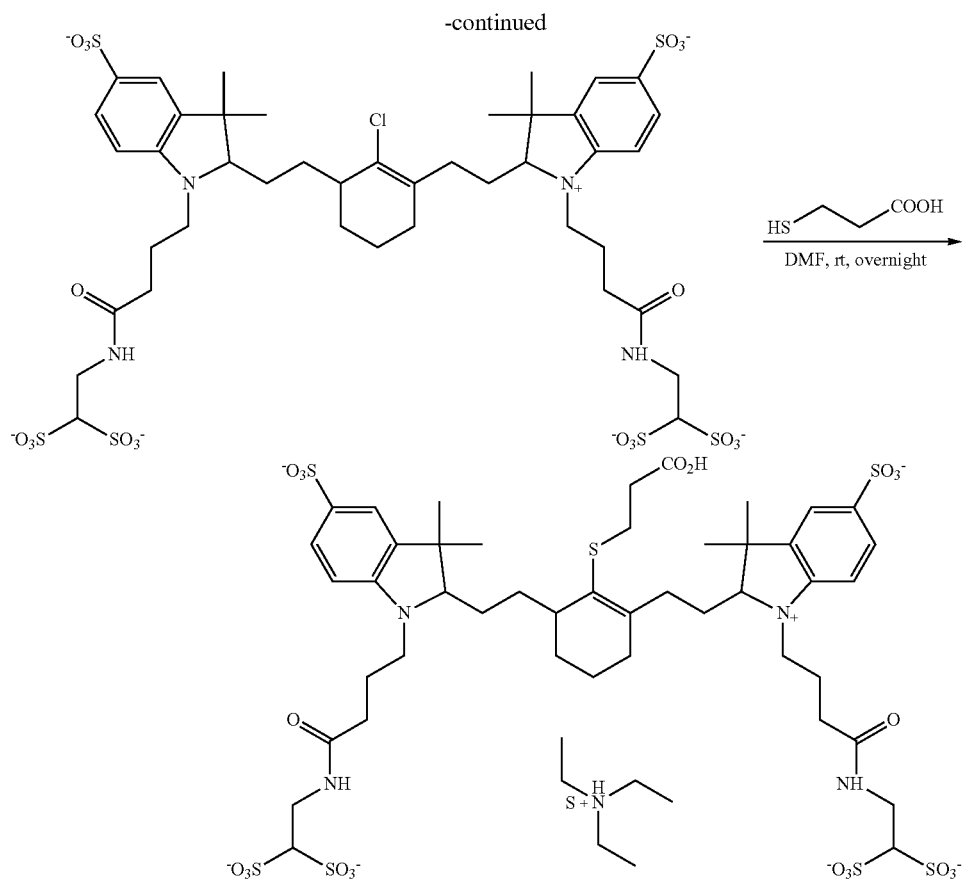

After a reaction was performed in the same manner as in Journal of Photochemistry and Photobiology A: Chemistry 168 (2004) 53-57 using Intermediate 18 prepared in the same manner as in the method of preparing Intermediate 2, Compound (60 mg, 27.5%) was prepared using an ion exchange resin.

11) Preparation of [Compound 43]

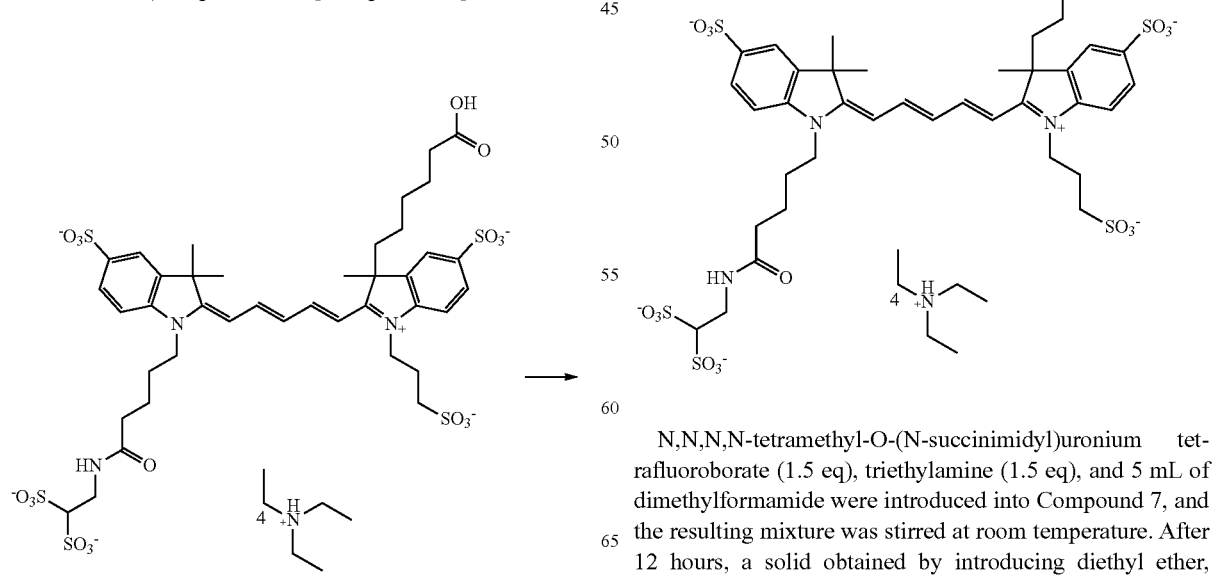

N,N,N,N-tetramethyl-O-(N-succinimidyl)uronium tetrafluoroborate (1.5 eq), triethylamine (1.5 eq), and 5 mL of dimethylformamide were introduced into Compound 7, and the resulting mixture was stirred at room temperature. After 12 hours, a solid obtained by introducing diethyl ether, precipitation and then filtration was subjected to ion exchange and reverse phase column chromatography to purify Compound 43 (3.7 mg, 76.2%).

12) Preparation of [Compound 44]

13) Preparation of [Compound 45]

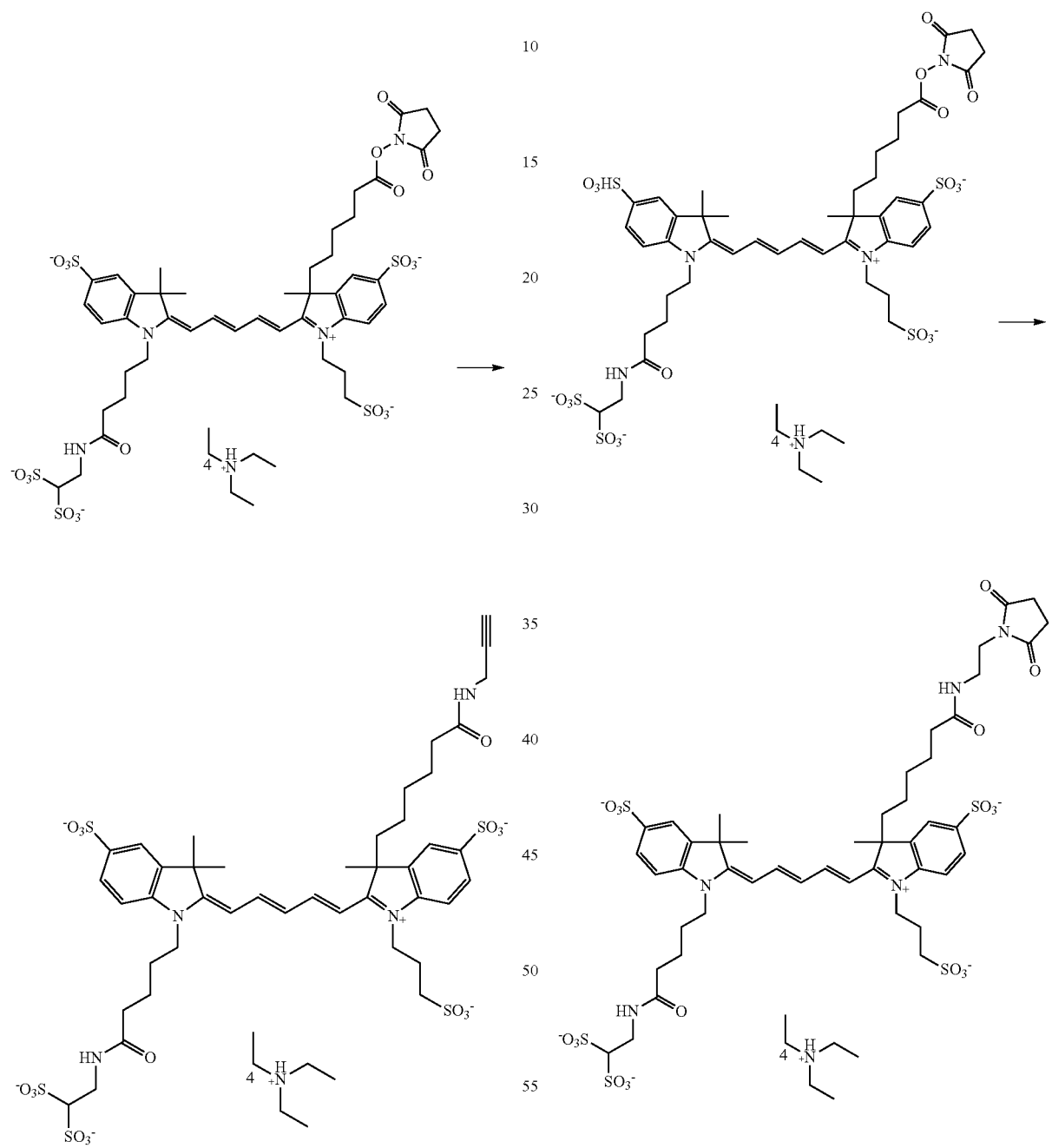

Compound 43, propargylamine (1.5 eq), triethylamine (1.5 eq), and 4.3 mL of dimethylformamide were introduced, and the resulting mixture was stirred at room temperature. After 5 hours, a solid obtained by introducing diethyl ether, precipitation and then filtration was subjected to ion exchange and reverse phase column chromatography to purify Compound 44 (2.7 mg, 81.3%).

Compound 43, N-(2-aminoethyl)maleimide trifluoroacetate salt (1.5 eq), triethylamine (1.5 eq), and 4.3 mL of dimethylformamide were introduced, and the resulting mixture was stirred at room temperature. After 16 hours, a solid obtained by introducing diethyl ether, precipitation and then filtration was subjected to ion exchange and reverse phase column chromatography to purify Compound 45 (1.9 mg, 67.9%).

14) Preparation of [Compound 52]

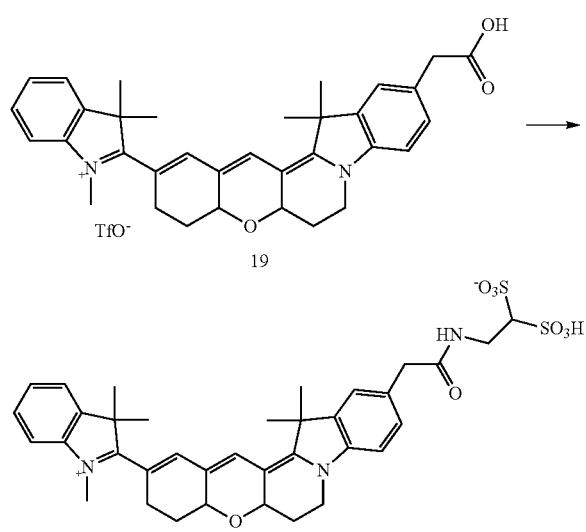

244 mg of Intermediate 19 (KR 2017-008700), 200 mg of ammonium 2-aminoethane-1,1-disulfonic acid hydrate, 108 mg of 1-(3-dimethylaminopropyl)-3-ethylcarbodiimide hydrochloride (EDC hydrochloride), and 76 mg of 1-hydroxybenzotriazole (HOBt) were introduced into 10 ml of dimethylformamide (DMF), and the resulting mixture was stirred at room temperature for 12 hours. Thereafter, the product was concentrated under reduced pressure and a solid was precipitated with ethylene acetate. The precipitated solid was subjected to reverse phase chromatography to prepare Compound 52 (170 mg, 51.3%).

15) Preparation of Phalloidin-Dye Conjugate

N,N-diisopropylethylamine (3 eq) was added to DMF (200 μL), aminophalloidin (1 mg), and a succinimidyl ester derivative (1.5 eq) of Compound 5, and the mixture was stirred at room temperature overnight. The solution was concentrated and dried under vacuum, and the residue was purified with column chromatography. The product effectively stains F-actin filaments in the preparation of fixed cells.

16) Preparation of Aminodextran-Dye Conjugate

Dye/dextran at a ratio of about 12 was obtained by adding Compound 43 to a 70,000 MW aminodextran solution including an average of 13 amino groups in 0.1 M sodium bicarbonate (400 μL). After 6 hours, the conjugate was purified with SEPHADEX G-50 using water as an eluent.

17) Preparation of Nucleotide-Dye Conjugate

DMF (2 mg, Sigma) and a succinimidyl ester derivative of Compound 1 in triethylamine (5 μL) were added to a solution of 5-(3-aminoallyl)-2-deoxyuridine 5'-triphosphate in H$_2$O (100 μL). The mixture was stirred at room temperature for 3 hours, and then concentrated and dried under vacuum. The residue was purified with HPLC. A dark blue nucleotide conjugate was obtained by lyophilizing the product fraction.

18) Preparation of Oligonucleotide-Dye Conjugate

A 5'-amine-modified 18-base M13 primer sequence (100 μg) in H$_2$O (4 μL) was added to a solution (pH=8.5) of Compound 36 (500 μg) in a 0.1 M sodium borate buffer (200 μL). The mixture was stirred at room temperature overnight, and 3 volumes of iced ethanol was added thereto. The mixture was cooled to −20° C. and centrifuged to isolate a supernatant, and the pellet was rinsed with ethanol, and then dissolved in H$_2$O (100 μL). A labeled oligonucleotide was purified with HPLC. A desired peak was collected and evaporated to obtain a fluorescent oligonucleotide.

19) Labeling of β-galactosidase

β-Galactosidase was put into a PBS buffer (1 mg in 200 μL), and the mixture was treated with a solution of Compound 45 (5 mg) in DMF (100 μL). Non-reactive dyes were removed by centrifugation.

EXPERIMENTAL EXAMPLES

Experimental Example 1

The photophysical properties of [Compound 7] obtained in the Preparation Examples were evaluated, and the results are shown in [Table 1]. The maximum absorption wavelength $\lambda_{abs,\ max}$), the maximum fluorescence wavelength ($\lambda_{PL,\ max}$), the molar extinction coefficient (ε at $\lambda_{max}$), and the quantum efficiency (Φ) were measured for each solvent. The measurement was performed in DMSO, ethanol (EtOH), methylene chloride (MC), water, and PBS, and the measurement results are shown in the following Table 1.

TABLE 1

| Classification | DMSO | EtOH | MC | Water | PBS |
|---|---|---|---|---|---|
| $\lambda_{abs,\ max}$/ | 656/ | 656/ | 666/ | 650/ | 650/ |
| ε at $\lambda_{max}$ | 201,000 | 232,000 | 155,000 | 227,000 | 230,000 |
| $\lambda$PL, $_{max}$/ | 685/ | 682/ | 685/ | 670/ | 669/ |
| Φ | 0.623 | 0.483 | — | 0.261 | 0.315 |

As shown in [Table 1], it can be confirmed that [Compound 7] of the present invention is dissolved in various solvents to show high extinction coefficients.

Experimental Example 2

After a 1 mg/ml protein solution was prepared by diluting Goat Anti-Mouse IgG with a 0.1 M sodium bicarbonate buffer, 125 μl of the protein solution was added to each of 5 tubes. A dye solution (5 mg/ml) including prepared Compound 7 was added to prepared tubes at 1, 2, 3, 4, and 5 μl, and the tubes were immediately vortexed. Subsequently, after the dye solutions were shaken at room temperature in a locker for 30 minutes, the reaction solutions were added to Amicon centrifuge filters. The reaction solutions were filtered with PBS until the free dye was removed by a centrifuge (14,000 rpm, 10 minutes, 5 times).

After inverting and binding the centrifuge filter to an Amicon tube, the filtrate was recovered (1000 rpm, 2 minutes) and then diluted with 1 ml of PBS, and then fluorescence was measured by UV, PL and a microplate reader.

The ratio of the dye to the protein was determined using the following equation.

$$\frac{D}{P} = \frac{A_{dye} \times E_{prot}}{(A_{280} - XA_{dye}) \times E_{dye}}$$

$A_{dye}$: Absorbance of dye at maximum absorption wavelength after labeling $A_{280}$: Absorbance at 280 nm $E_{prot}$: Molecular extinction coefficient (210,000 in the case of IgG) of protein at 280 nm $E_{dye}$: Molecular extinction coefficient of dye at maximum absorption wavelength X: Absorbance at 280 nm/absorbance of Compound 2 at maximum absorption wavelength FIGS. 1 and 2 are graphs comparing the normalized maximum absorption wavelength and the normalized maximum fluorescence wavelength of each of antibody conjugates having similar D/P ratios.

Referring to FIG. 1, it can be seen that the antibody conjugate labeled with [Compound 7] has a maximum absorption wavelength similar to those of conjugates labeled with Alexa Fluor 647 and Cy5. Further, from the H band, it can be confirmed that [Compound 7] has a smaller degree of aggregation than those of conjugates labeled with Alexa Fluor 647 and Cy5.

Figure 2:
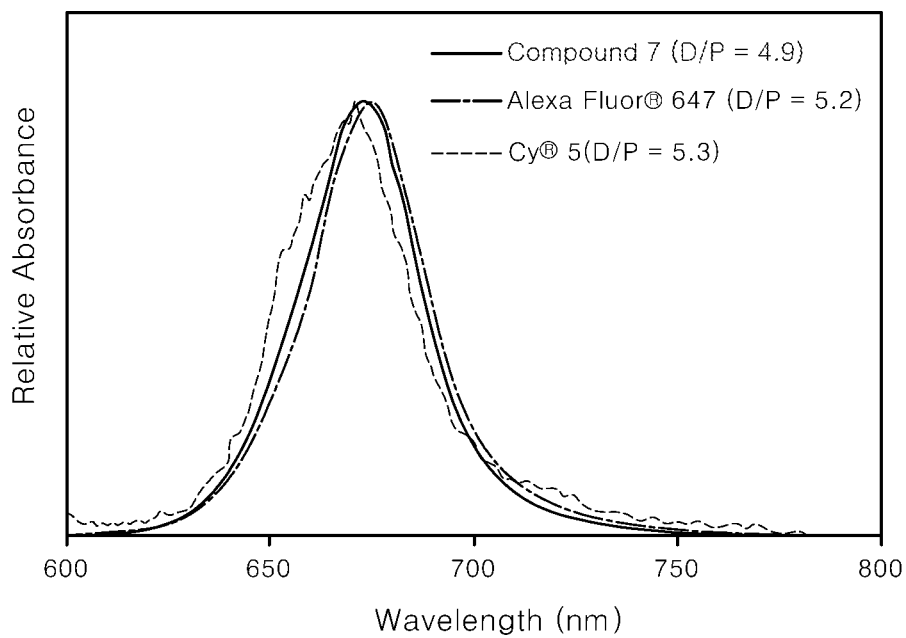

Referring to FIG. 2, it can be seen that the antibody conjugate labeled with [Compound 7] has a maximum fluorescence wavelength similar to those of conjugates labeled with Alexa Fluor 647 and Cy5.

Figure 3:
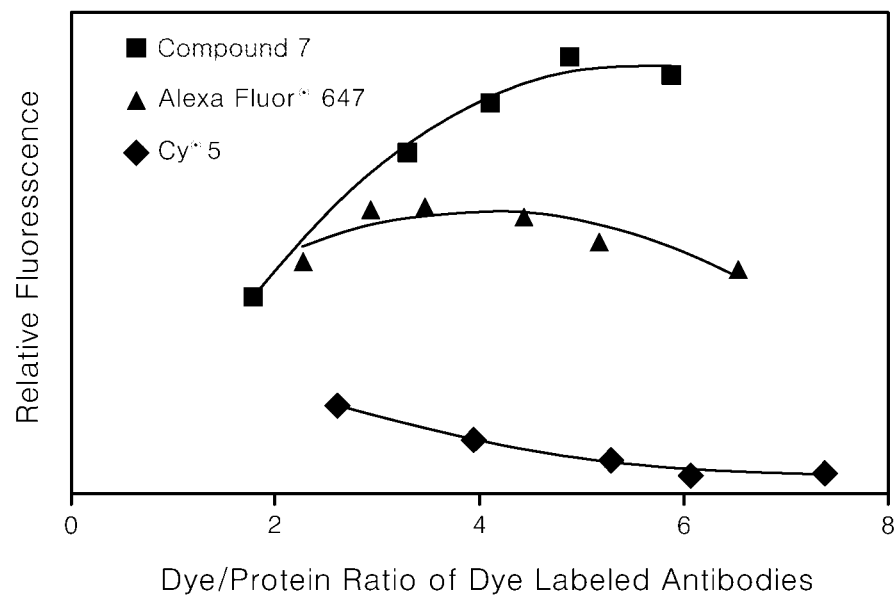
FIG. 3 is a graph comparing the relative fluorescent intensities of Goat Anti-Mouse IgG labeled with each of [Compound 7], Alexa Fluor 647, and Cy5 according to the D/P ratio.

FIG. 3 is a graph comparing the relative fluorescent intensities of Goat Anti-Mouse IgG labeled with each of [Compound 7], Alexa Fluor 647, and Cy5 according to the D/P ratio.

Referring to FIG. 3, it can be seen that the antibody conjugate labeled with [Compound 7] has a maximum fluorescent intensity at a D/P ratio of about 5. In addition, it was confirmed that the antibody conjugate labeled with [Compound 7] had a much higher fluorescent intensity than those of the antibody conjugate labeled with Alexa Fluor 647 and Cy5 at a D/P ratio or 3 or more.

In the above-described Experimental Example 2), the same experiment was performed using Goat anti-Rabbit IgG instead of Goat Anti-Mouse IgG.

Figure 4:
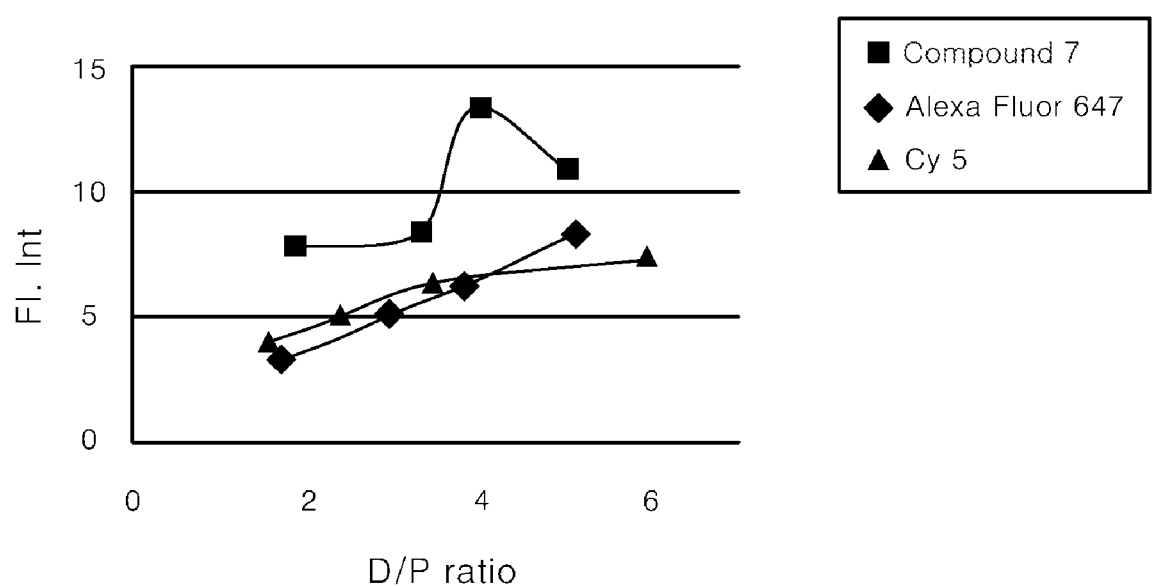
FIG. 4 is a graph comparing the relative fluorescent intensities of Goat anti-Rabbit IgG labeled with each of [Compound 7], Alexa Fluor 647, and Cy5 according to the D/P ratio.

FIG. 4 is a graph comparing the relative fluorescent intensities of Goat anti-Rabbit IgG labeled with each of [Compound 7], Alexa Fluor 647, and Cy5 according to the D/P ratio.

Referring to FIG. 4, it can be seen that the antibody conjugate labeled with [Compound 7] has a maximum fluorescent intensity at a D/P ratio of about 4. Further, it was confirmed that the antibody conjugate labeled with [Compound 7] had a much higher fluorescent intensity than those of the antibody conjugate labeled with Alexa Fluor 647 and Cy5.

In the above-described Experimental Example 2), the same experiment was performed using Goat anti-Human IgG instead of Goat Anti-Mouse IgG.

Figure 5:
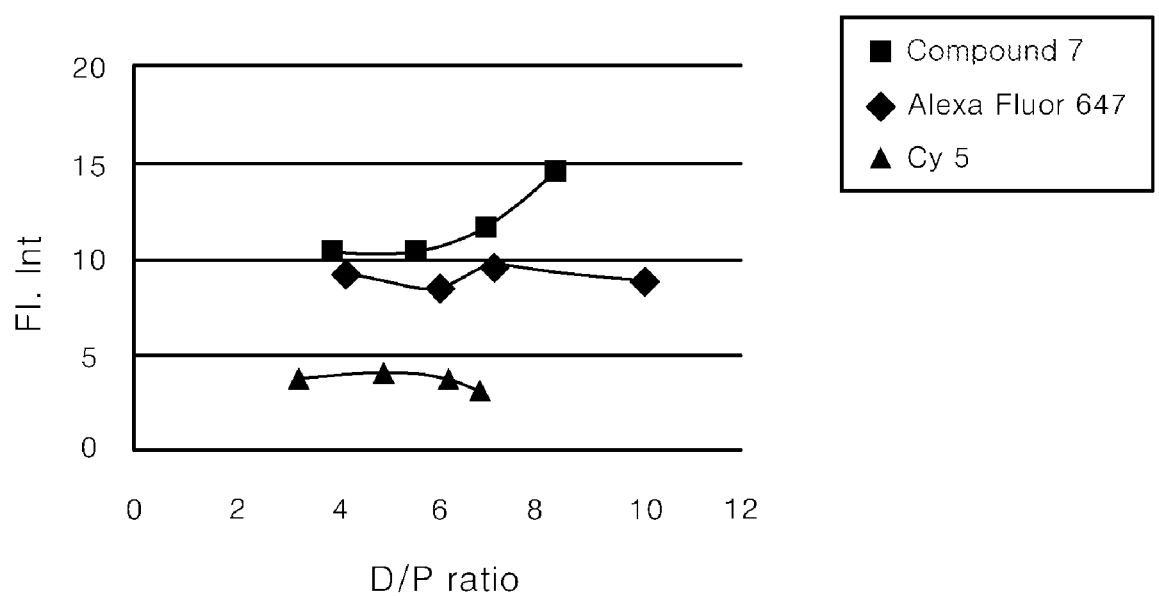
FIG. 5 is a graph comparing the relative fluorescent intensities of Goat anti-Human IgG labeled with each of [Compound 7], Alexa Fluor 647, and Cy5 according to the D/P ratio.

FIG. 5 is a graph comparing the relative fluorescent intensities of Goat anti-Human IgG labeled with each of [Compound 7], Alexa Fluor 647, and Cy5 according to the D/P ratio.

Referring to FIG. 5, it can be seen that the antibody conjugate labeled with [Compound 7] has a maximum fluorescent intensity at a D/P ratio of about 8. In addition, it was confirmed that the antibody conjugate labeled with [Compound 7] had a higher fluorescent intensity than those of the antibody conjugate labeled with Alexa Fluor 647 and Cy5.

Figure 6:
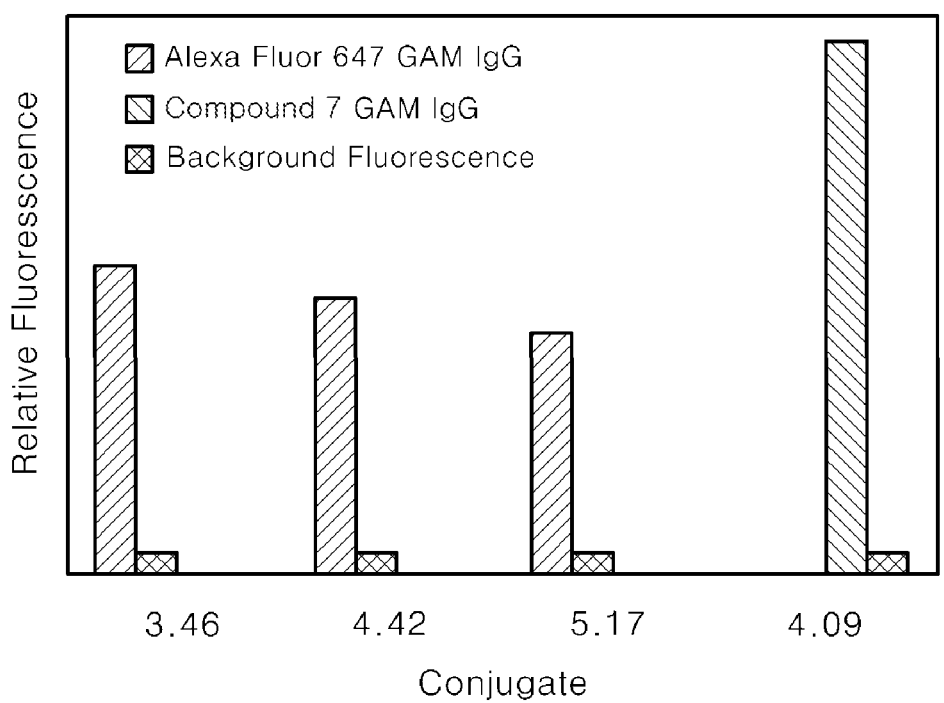
FIG. 6 is a graph comparing the fluorescent light emissions of Alexa Fluor 647 GAM IgG, Compound 7 GAM IgG, and background fluorescence.

FIG. 6 is a graph comparing the fluorescent light emissions of Alexa Fluor 647 GAM IgG, Compound 7 GAM IgG, and background fluorescence, and fluorescence was measured by the method according to Experimental Example 2).

Referring to FIG. 6, it was proved that the Compound 7 GAM conjugate was much brighter than the Alexa Fluor 647 GAM conjugate.

Experimental Example 3

After a 10 ug/ml solution was prepared by dissolving IgG from Mouse Serum (primary) in a coating buffer, 100 μl of the solution was dispensed into each well of a FLISA H/B black Corning plate, and then the plate was top-sealed and incubated in a dark room at room temperature for 2 hours. Subsequently, 300 μl of a washing buffer was dispensed into each well and washing was performed three times, 300 μl of a blocking buffer was dispensed into each well, and the plate was top-sealed and then incubated in a dark room at room temperature for 1 hour. Next, after the blocking buffer was removed, washing was performed three times with a washing buffer, 100 μl of a dye-conjugated secondary antibody (10 ug/ml) was dispensed into each well, the plate was top-sealed and then incubated in a dark room at room temperature for 1 hour, and after the solution was removed, 200 μl of a washing buffer was dispensed into each well, and washing was performed five times. Subsequently, 100 μl of PBS was dispensed into each well containing the sample, and then fluorescence was measured by a microplate reader.

Figure 7:
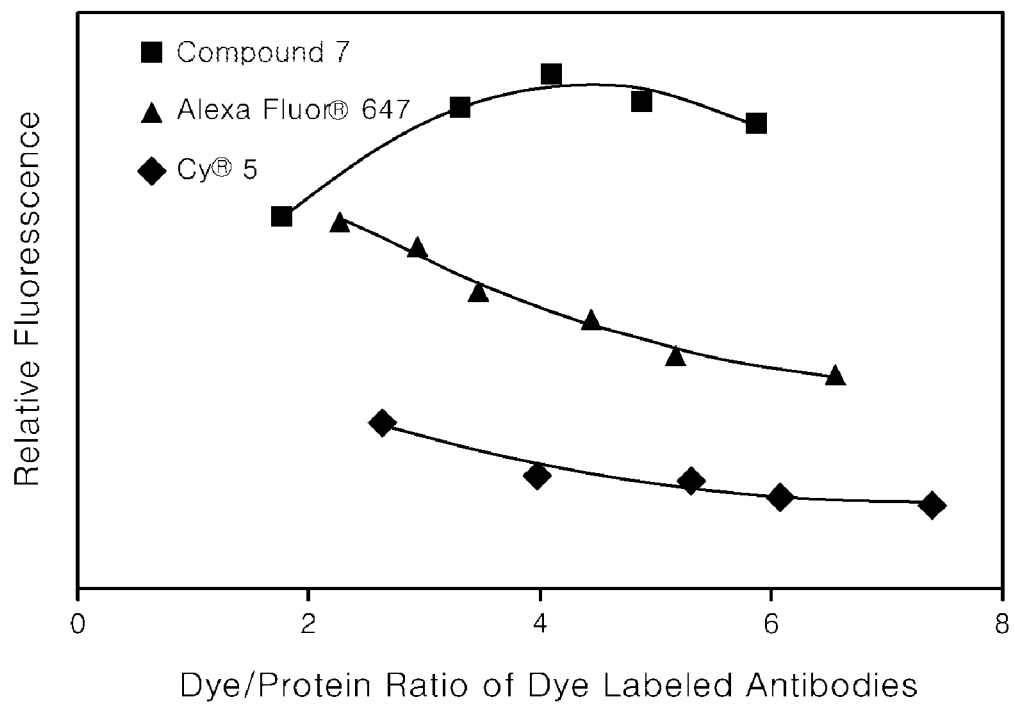
FIG. 7 is a graph comparing the relative fluorescent intensities of Goat Anti-Mouse IgG labeled with each of [Compound 7], Alexa Fluor 647, and Cy5 according to the D/P ratio using FLISA after antigen-antibody formation with Mouse IgG.

FIG. 7 is a graph comparing the relative fluorescent intensities of Goat Anti-Mouse IgG labeled with each of [Compound 7], Alexa Fluor 647, and Cy5 according to the D/P ratio using FLISA after antigen-antibody formation with Mouse IgG.

Referring to FIG. 7, it can be seen that the antibody conjugate labeled with ([Compound 7]) has a maximum fluorescence intensity at a D/P ratio of about 4. In addition, it was confirmed that the antibody conjugate labeled with [Compound 7] had a much higher fluorescent intensity than those of the antibody conjugate labeled with Alexa Fluor 647 and Cy5 at a D/P ratio or 3 or more.

Experimental Example 4

Lymphocytes were obtained from the spleen of a naïve C57BL/6 mouse (5 weeks old). After the spleen was placed on a metal screen, the spleen was mashed up with a plunger and the red blood cells were lysed with 0.83% ammonium chloride for 2 minutes. Thereafter, a suspension was prepared by dispersing the lymphocytes in Hyclone™RPMI 1640 (GE Healthcare Life Science) including 1% fetal bovine serum and 1% penicillin/streptomycin.

The isolated lymphocytes were stained with a biotinylated anti-mouse CD8 antibody (Biolegend) per 1×10^6 cells at a ratio (1:400) in a light-shielded state at 4° C. for 30 minutes. Thereafter, the lymphocytes were stained with Control Streptavidin-APC (1:1,000), SA-Cy5® (the same ratio), SA-Alexa Fluor® 647 (the same ratio), and SA-Compound 7(the same ratio) under the same conditions (4° C., in a light-shielded state) for 30 minutes. A suspension was prepared by dispersing stained cells in a FACS buffer (3% FBS, 0.1% sodium azide in PBS) and analyzed by flow cytometry.

Figure 8:
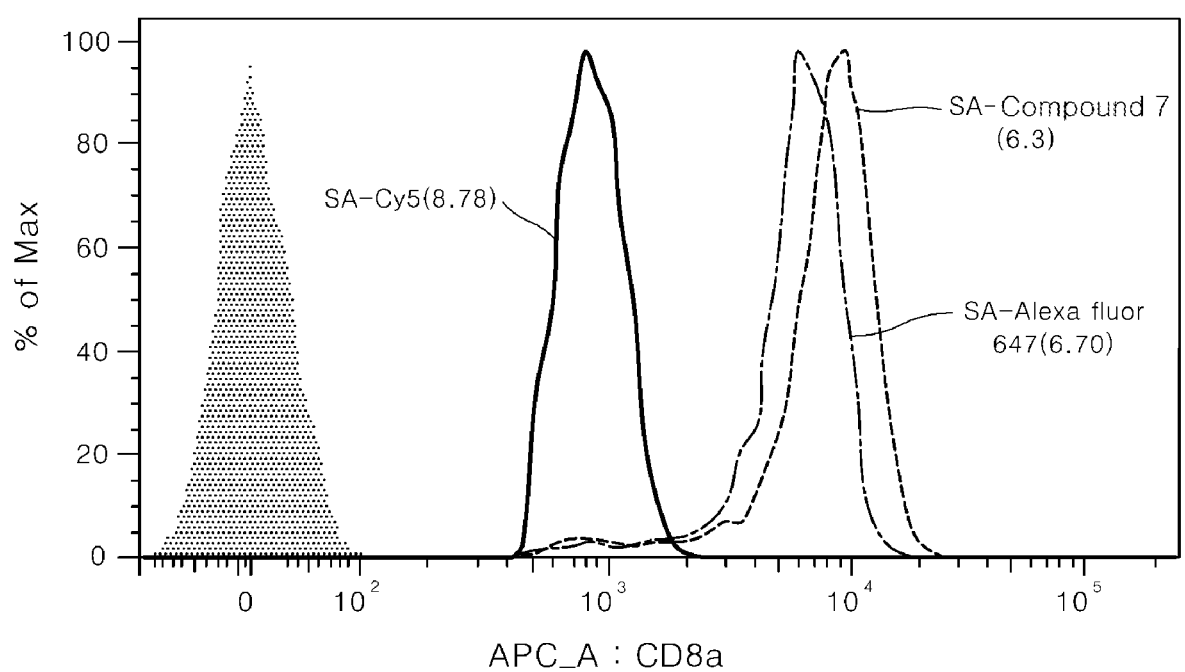
FIG. 8 is a graph illustrating flow cytometry analysis of fluorescent brightness.

FIG. 8 is a graph illustrating flow cytometry analysis of fluorescent brightness.

Referring to FIG. 8, it can be confirmed that among SA-Cy5® (DOL=8.78), SA-Alexa Fluor® 647 (DOL=6.70), and SA-Compound 7 (DOL=6.38), SA-Compound 7 is at least 10-fold brighter than SA-Cy5 and is a little brighter than SA-Alexa Fluor 647, and SA-Compound 7 is the brightest.

Experimental Example 5

3 uM (in PBS buffer, pH 7.4) of each of Cy5®, Alexa Fluor® 647, and Compound 7 were each continuously irradiated with light for 16 hours, and UV spectra were measured (using a Lumencor® product, white source, intensity 10%). The initial absorbance intensities were normalized and compared.

Figure 9:
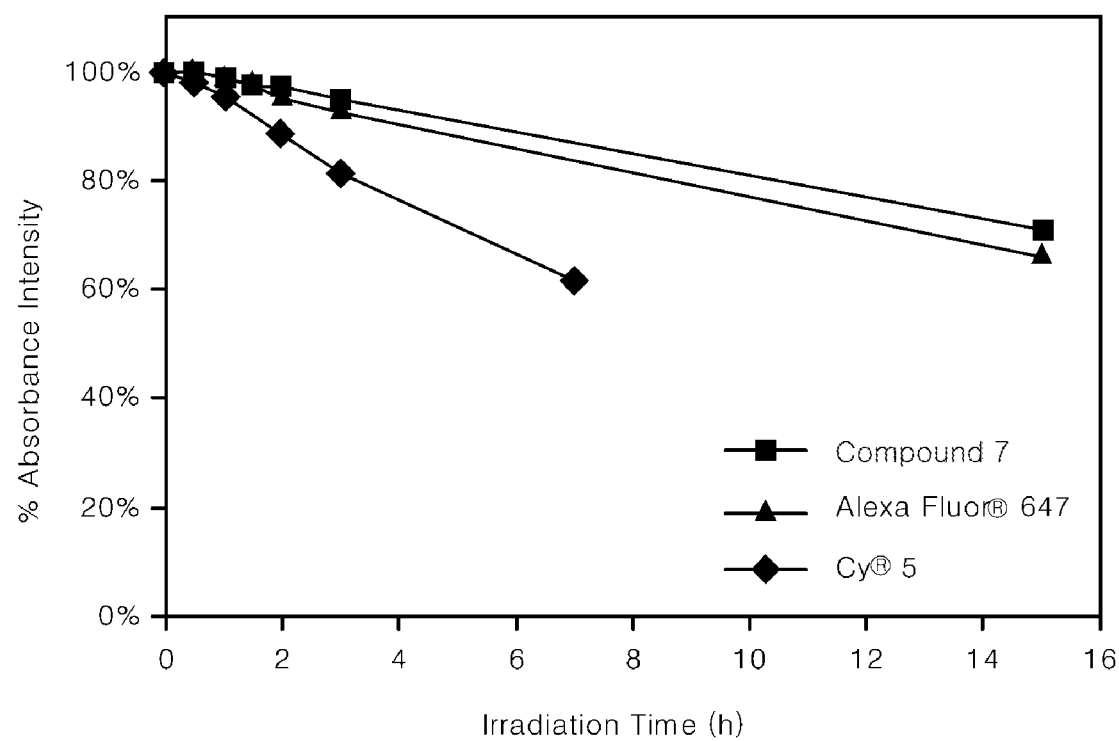
FIG. 9 is a graph comparing the photobleaching of each of [Compound 7], AlexaFluor647, and Cy5.

FIG. 9 is a graph comparing the photobleachings of each of [Compound 7], AlexaFluor647, and Cy5.

Referring to FIG. 9, it was confirmed that as time elapsed, all the three dyes showed a tendency of the initial absorbance intensity to decrease, but when the degrees of decrease in absorbance intensity over time were compared, Compound 7 was better than Cy5 due to a much smaller degree of decrease, and was at a level equivalent to and higher than Alexa Fluor 647.

Experimental Example 6

The photophysical properties of [Compound 10] obtained in the Preparation Examples were evaluated, and the results are shown in [Table 2]. The maximum absorption wavelength ($\lambda_{abs, max}$), the maximum fluorescence wavelength ($\lambda_{PL, max}$), and the molar extinction coefficient ($\varepsilon$ at $\lambda_{max}$) were measured for each solvent. The measurement was performed in DMSO, ethanol (EtOH), methylene chloride (MC), water, and PBS, and the measurement results are shown in the following Table 2.

TABLE 2

| Classification | DMSO | EtOH | MC | Water | PBS |
|---|---|---|---|---|---|
| $\lambda_{abs, max}$/ | 770/ | 758/ | 772/ | 750/ | 750/ |
| $\varepsilon$ at $\lambda_{max}$ | 176,000 | 205,000 | 152,000 | 204,000 | 202,000 |
| $\lambda$PL, max | 799 | 789 | 796 | 778 | 778 |

As shown in [Table 2], it can be confirmed that [Compound 10] of the present invention is dissolved in various solvents to show high extinction coefficients, and exhibits a maximum absorption wavelength and a maximum fluorescence wavelength at 700 or more, respectively.

Experimental Example 7

The photophysical properties [Compound 46] to [Compound 51] obtained in the Preparation Examples were evaluated, and the evaluation results are shown in the following [Table 3]. The maximum absorption wavelength ($\lambda_{abs, max}$), the maximum fluorescence wavelength ($\lambda_{PL, max}$), the molar extinction coefficient ($\varepsilon$ at $\lambda_{max}$), and the quantum efficiency ($\Phi$) were measured for each solvent. The measurement was performed in DMSO, ethanol (EtOH), methylene chloride (MC), water, and PBS, and the measurement results are shown in the following Table 3.

TABLE 3

| Classification | | DMSO | EtOH | MC | Water | PBS |
|---|---|---|---|---|---|---|
| Compound 46 | $\lambda_{abs, max}$/ | 572/ | 572/ | 572/ | 562/ | 562/ |
| | $\varepsilon$ at $\lambda_{max}$ | 132,000 | 134,000 | 142,000 | 140,000 | 145,000 |
| | $\lambda_{PL, max}$/ | 589/ | 588/ | 584/ | 576/ | 576/ |
| | $\Phi$ | — | — | — | — | — |
| Compound 47 | $\lambda_{abs, max}$/ | 584/ | 580/ | 584/ | 572/ | 572/ |
| | $\varepsilon$ at $\lambda_{max}$ | 97,000 | 103,000 | 102,000 | 62,000 | 56,000 |
| | $\lambda_{PL, max}$/ | 596/0.730 | 589/ | 593/ | 581/0.784 | 581/0.803 |
| | $\Phi$ | | | | | |
| Compound 48 | $\lambda_{abs, max}$/ | 566/ | 564/ | 564/ | 556/ | 556/ |
| | $\varepsilon$ at $\lambda_{max}$ | 91,000 | 91,000 | 110,000 | 96,000 | 98,000 |
| | $\lambda_{PL, max}$/ | 582/ | 579/ | 578/ | 569/ | 569/ |
| | $\Phi$ | — | — | — | — | — |
| Compound 49 | $\lambda_{abs, max}$/ | 534/ | 528/ | 534/ | 522/ | 522/ |
| | $\varepsilon$ at $\lambda_{max}$ | 63,000 | 68,000 | 78,000 | 67,000 | 69,000 |
| | $\lambda_{PL, max}$/ | 552/ | 546/ | 548/ | 538/ | 538/ |
| | $\Phi$ | — | — | — | — | — |
| Compound 50 | $\lambda_{abs, max}$/ | 530/ | 526/ | 532/ | 520/ | 520/ |
| | $\varepsilon$ at $\lambda_{max}$ | 98,000 | 103,000 | 118,000 | 104,000 | 108,000 |
| | $\lambda_{PL, max}$/ | 549/ | 543/ | 546/ | 537/ | 537/ |
| | $\Phi$ | — | — | — | — | — |
| Compound 51 | $\lambda_{abs, max}$/ | 670/ | 666/ | 676/ | 656/ | 656/ |
| | $\varepsilon$ at $\lambda_{max}$ | 217,000 | 228,000 | 239,000 | 218,000 | 226,000 |
| | $\lambda_{PL, max}$/ | 691/ | 685/ | 692/ | 676/ | 677/ |
| | $\Phi$ | — | — | — | — | — |

As shown in [Table 3], it can be confirmed that [Compound 46] to [Compound 51] of the present invention exhibit a maximum absorption wavelength and a maximum fluorescence wavelength at 500 or more, respectively.

The embodiments of the present invention have been described with reference to the accompanying drawings, but the present invention is not limited to the embodiments and may be prepared in various forms, and a person with ordinary skill in the art to which the present invention pertains will understand that the present invention can be implemented in another specific form without changing the technical spirit or essential feature of the present invention. Therefore, it should be understood that the above-described embodiments are only exemplary in all aspects and are not restrictive.

The invention claimed is:

1. A labeling dye represented by the following [Chemical Formula 1] or [Chemical Formula 2]:

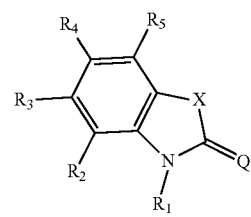

[Chemical Formula 1]

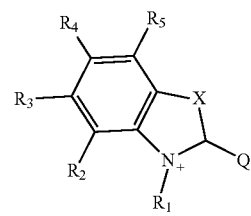

[Chemical Formula 2]

in [Chemical Formula 1] or [Chemical Formula 2],

X is $CR_6R_7$, S, or O,

Q is a polymethine in which a ring selectively including at least one heteroatom selected from nitrogen, oxygen, and sulfur is substituted, or a polyene in which a ring selectively including at least one heteroatom selected from nitrogen, oxygen, and sulfur is substituted, $R_1$ is selected from the following [Chemical Formula 3] to [Chemical Formula 5], or -L-X functional group, $R_2$ to $R_7$ are each independently selected from hydrogen, deuterium, a substituted or unsubstituted C1-C10 alkyl, a substituted or unsubstituted C1-C10 heteroalkyl including at least one heteroatom, a substituted or unsubstituted C2-C10 alkenyl, a substituted or unsubstituted C2-C10 alkynyl, a substituted or unsubstituted C1-C10 alkoxy, a substituted or unsubstituted aryloxy, a substituted or unsubstituted C1-C10 haloalkyl, a halogen, cyano, hydroxyl, a substituted or unsubstituted amino, a substituted or unsubstituted amide, carbamates, sulfhydryl, nitro, carboxyl, carboxylates, a substituted or unsubstituted aryl, a substituted or unsubstituted heteroaryl, a substituted or unsubstituted aralkyl, quaternary ammonium, phosphoric acid, phosphates, ketones (—CO), aldehydes, esters (—COO), acyl chloride, sulfonic acid, sulfonates, hydrazine, thiols, acetals, ketals, phosphonates (phosphites), hypophosphite, sulfohydroxyl, sulfates, azido, guanidium, carbonyl, thiocarbonyl, aminothiocarbonyl, polyalkylene oxides, a -L-X functional group, a -L-Z functional group, and the following [Chemical Formula 3] to [Chemical Formula 5], or two or more selected from $R_1$ to $R_7$ are linked to each other to form a fused ring, L is a linker including 1 to 150 non-hydrogen atoms, X is a reactive group selected from carboxyl, succinimidyl ester, sulfo-succinimidyl ester, isothiocyanate, maleimide, haloacetamide, hydrazide, vinyl sulphone, dichlorotriazine, phosphoramidite, alkyl halides, acyl halides, carbohydrazide, hydroxylamine, ketones, alkynes, azide, aliphatic and aromatic amines, sulfotetrafluorophenyl ester, sulfodichlorophenyl ester, carbonyl azide, sulfonyl chloride, sulfonyl fluoride, boronic acid, isocyanate, a halogen-substituted triazine, a halogen-substituted pyridine, a halogen-substituted diazine, tetrafluorophenyl ester, imido ester, azidonitrophenyl, glyoxal, and aldehydes, Z is a fluorophore capable of generating a fluorescence signal, at least one or more of $R_1$ to $R_7$ are one selected from the following [Chemical Formula 3] to [Chemical Formula 5],

[Chemical Formula 3]

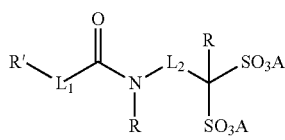

[Chemical Formula 4]

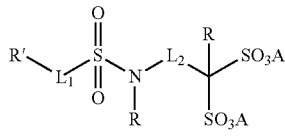

[Chemical Formula 5]

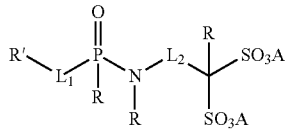

in [Chemical Formula 3] to [Chemical Formula 5], $L_1$ is a linker including 1 to 150 non-hydrogen atoms, $L_1$ in [Chemical Formula 3] to [Chemical Formula 5] is present or not present, $L_2$ is a C1-C20 alkylene, or a C1-C20 heteroalkylene including at least one heteroatom, A is hydrogen or $M^+$ ($M^+$ is a counter ion), R is selected from hydrogen, a substituted or unsubstituted C1-C10 alkyl, a substituted or unsubstituted C1-C10 heteroalkyl including at least one heteroatom, a substituted or unsubstituted C2-C10 alkenyl, a substituted or unsubstituted C2-C10 alkynyl, a substituted or unsubstituted C1-C10 alkoxy, and a substituted or unsubstituted C1-C10 haloalkyl, R' represents a site bonded to at least one of $R_1$ to $R_7$, and at least one or more of R and $R_1$ to $R_7$ are a -L-X functional group.

2. The labeling dye of claim 1, wherein two or more selected from $R_2$ to $R_5$ are linked to each other to form a fused ring, and the fused ring is a substituted or unsubstituted aliphatic fused ring; a substituted or unsubstituted aromatic fused ring; a substituted or unsubstituted aliphatic hetero fused ring comprising one or more of N, O, and S atoms; a substituted or unsubstituted aromatic hetero fused ring comprising one or more of N, O, and S atoms; a substituted or unsubstituted fused ring of an aliphatic ring and an aromatic ring; a substituted or unsubstituted fused ring of an aliphatic hetero ring comprising one or more of N, O, and S atoms and an aromatic hetero ring comprising one or more of N, O, and S atoms; a substituted or unsubstituted fused ring of a hydrocarbon ring and a hetero ring comprising one or more of N, O, and S atoms; or a substituted or unsubstituted C60-C84 fullerene.

3. The labeling dye of claim 1, wherein Z is a fluorophore selected from structures displayed by coumarins, cyanine, BODIPY, fluoresceins, rhodamines, pyrenes, carbopyronin, oxazines, xanthenes, thioxanthene, acridines, or a fluorophore selected from a structure represented by [Chemical Formula 1] or [Chemical Formula 2].

4. The labeling dye of claim 1, wherein at least one or more of $R_2$ to $R_5$ are selected from [Chemical Formula 3] to [Chemical Formula 5].

5. The labeling dye of claim 1, wherein at least one or more of $R_6$ and $R_7$ are selected from [Chemical Formula 3] to [Chemical Formula 5].

6. The labeling dye of claim 1, wherein any carbon in the polymethine or the polyene is substituted with a substituent selected from hydrogen, deuterium, a substituted or unsubstituted C1-C10 alkyl, a substituted or unsubstituted C1-C10 heteroalkyl comprising at least one heteroatom, a substituted or unsubstituted C2-C10 alkenyl, a substituted or unsubstituted C2-C10 alkynyl, a substituted or unsubstituted C1-C10 alkoxy, a substituted or unsubstituted aryloxy, a substituted or unsubstituted C1-C10 haloalkyl, a halogen, cyano, hydroxyl, a substituted or unsubstituted amino, a substituted or unsubstituted amide, carbamates, sulfhydryl, nitro, carboxyl, carboxylates, a substituted or unsubstituted aryl, a substituted or unsubstituted heteroaryl, a substituted or unsubstituted aralkyl, quaternary ammonium, phosphoric acid, phosphates, ketones (—CO), aldehydes, esters (—COO), acyl chloride, sulfonic acid, sulfonates, hydrazine, thiols, acetals, ketals, phosphonates (phosphites), hypophosphite, sulfohydroxyl, sulfates, azido, guanidium, carbonyl, thiocarbonyl, aminothiocarbonyl, polyalkylene oxides, a -L-X functional group, a -L-Z functional group, and [Chemical Formula 3] to [Chemical Formula 5].

7. The labeling dye of claim 6, wherein adjacent substituents in the polymethine or the polyene are linked to each other to form a ring.

8. The labeling dye of claim 6, wherein a substituent in the polymethine or the polyene and a substituent selected from $R_1$ to $R_7$ of [Chemical Formula 1] or [Chemical Formula 2] are linked to each other to form a ring.

9. The labeling dye of claim 6, wherein adjacent substituents in the polymethine or the polyene are linked to each other to form a ring, and
   a substituent in the polymethine or the polyene and a substituent selected from $R_1$ to $R_7$ of [Chemical Formula 1] or [Chemical Formula 2] are linked to each other to form a ring.

10. The labeling dye of claim 1, wherein the dye labels at least one biomolecule selected from antibodies, lipids, proteins, peptides, carbohydrates, and nucleic acids.

11. The labeling dye of claim 1, wherein the dye labels at least one selected from a drug, a hormone, a water-soluble vitamin, a fat-soluble vitamin, a mineral, a receptor, an enzyme, an enzyme substrate, a cell, cell membranes, toxins, microorganisms, polystyrene, and a microsphere, which include at least one selected from amino, sulfhydryl, carbonyl, hydroxyl, carboxyl, phosphate and thiophosphate.

12. A labeling kit comprising the labeling dye according to claim 1.

13. A labeling dye represented by the following [Chemical Formula 1] or [Chemical Formula 2]:

[Chemical Formula 1]

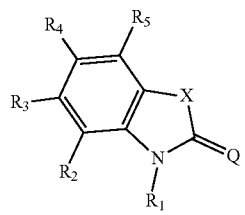

[Chemical Formula 2]

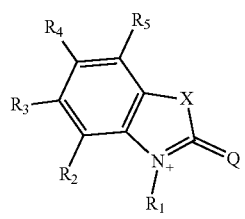

in [Chemical Formula 1] or [Chemical Formula 2],
X is $CR_6R_7$, S, or O,
Q is a polymethine in which a ring selectively including at least one heteroatom selected from nitrogen, oxygen, and sulfur is substituted, or a polyene in which a ring selectively including at least one heteroatom selected from nitrogen, oxygen, and sulfur is substituted,
wherein any carbon in the polymethine or the polyene is substituted with a -L-Z functional group,
$R_1$ to $R_7$ are each independently selected from hydrogen, deuterium, a substituted or unsubstituted C1-C10 alkyl, a substituted or unsubstituted C1-C10 heteroalkyl including at least one heteroatom, a substituted or unsubstituted C2-C10 alkenyl, a substituted or unsubstituted C2-C10 alkynyl, a substituted or unsubstituted C1-C10 alkoxy, a substituted or unsubstituted aryloxy, a substituted or unsubstituted C1-C10 haloalkyl, a halogen, cyano, hydroxyl, a substituted or unsubstituted amino, a substituted or unsubstituted amide, carbamates, sulfhydryl, nitro, carboxyl, carboxylates, a substituted or unsubstituted aryl, a substituted or unsubstituted heteroaryl, a substituted or unsubstituted aralkyl, quaternary ammonium, phosphoric acid, phosphates, ketones (—CO), aldehydes, esters (—COO), acyl chloride, sulfonic acid, sulfonates, hydrazine, thiols, acetals, ketals, phosphonates (phosphites), hypophosphite, sulfohydroxyl, sulfates, azido, guanidium, carbonyl, thiocarbonyl, aminothiocarbonyl, polyalkylene oxides, a -L-X functional group, a -L-Z functional group, and the following [Chemical Formula 3] to [Chemical Formula 5], or two or more selected from $R_1$ to $R_7$ are linked to each other to form a fused ring, L is a linker including 1 to 150 non-hydrogen atoms,
X is a reactive group selected from carboxyl, succinimidyl ester, sulfo-succinimidyl ester, isothiocyanate, maleimide, haloacetamide, hydrazide, vinyl sulphone, dichlorotriazine, phosphoramidite, alkyl halides, acyl halides, carbohydrazide, hydroxylamine, ketones, alkynes, azide, aliphatic and aromatic amines, sulfotetrafluorophenyl ester, sulfodichlorophenyl ester, carbonyl azide, sulfonyl chloride, sulfonyl fluoride, boronic acid, isocyanate, a halogen-substituted triazine, a halogen-substituted pyridine, a halogen-substituted diazine, tetrafluorophenyl ester, imido ester, azidonitrophenyl, glyoxal, and aldehydes,
Z is a fluorophore capable of generating a fluorescence signal, and is selected from structures displayed by coumarins, cyanine, BODIPY, fluoresceins, rhodamines, pyrenes, carbopyronin, oxazines, xanthenes, thioxanthene, acridines, or a fluorophore selected from a structure represented by [Chemical Formula 1] or [Chemical Formula 2],
at least one or more of $R_1$ to $R_7$ are one selected from the following [Chemical Formula 3] to [Chemical Formula 5],

[Chemical Formula 3]

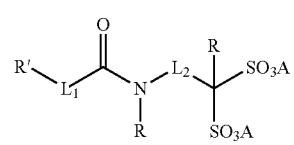

[Chemical Formula 4]

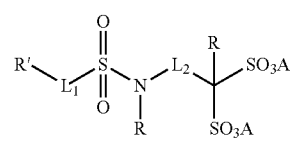

[Chemical Formula 5]

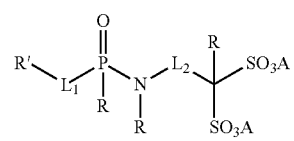

in [Chemical Formula 3] to [Chemical Formula 5],
$L_1$ is a linker including 1 to 150 non-hydrogen atoms,
$L_1$ in [Chemical Formula 3] to [Chemical Formula 5] is present or not present,
$L_2$ is a C1-C20 alkylene, or a C1-C20 heteroalkylene including at least one heteroatom, A is hydrogen or $M^+$ ($M^+$ is a counter ion), R is selected from hydrogen, a substituted or unsubstituted C1-C10 alkyl, a substituted or unsubstituted C1-C10 heteroalkyl including at least one heteroatom, a substituted or unsubstituted C2-C10 alkenyl, a substituted or unsubstituted C2-C10 alkynyl, a substituted or unsubstituted C1-C10 alkoxy, and a substituted or unsubstituted C1-C10 haloalkyl, R' represents a site bonded to at least one of $R_1$ to $R_7$, and at least one or more of R and $R_1$ to $R_7$ are a -L-X functional group.

14. The labeling dye of claim 13, wherein a substituent in the polymethine or the polyene and a substituent selected from $R_1$ of [Chemical Formula 1] or $R_1$ of [Chemical Formula 2] are linked to each other to form a ring.

15. The labeling dye of claim 14, wherein Z is the fluorophore selected from cyanine, or a structure represented by [Chemical Formula 1] or [Chemical Formula 2].

16. The labeling dye of claim 15, wherein a substituent in the polymethine or the polyene and a substituent selected from $R_1$ of [Chemical Formula 1] or $R_1$ of [Chemical Formula 2] are linked to each other to form a ring.

17. The labeling dye of claim 15, wherein a substituent in the polymethine or the polyene and a substituent in L of the -L-Z functional group are linked to each other to form a ring, and wherein a substituent in L of the -L-Z functional group and a substituent of cyanine, [Chemical Formula 1] or [Chemical Formula 2] of -L-Z functional group are linked to each other to form a ring.

\* \* \* \* \*